United States Patent
Milton et al.

(10) Patent No.: US 8,212,015 B2
(45) Date of Patent: *Jul. 3, 2012

(54) MODIFIED NUCLEOSIDES AND NUCLEOTIDES AND USES THEREOF

(75) Inventors: John Milton, Waldon (GB); Xiaohai Liu, Walden (GB)

(73) Assignee: Illumina Cambridge Limited, Nr. Saffron Walden, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/899,423

(22) Filed: Oct. 6, 2010

(65) Prior Publication Data

US 2011/0020827 A1 Jan. 27, 2011

Related U.S. Application Data

(63) Continuation of application No. 12/586,385, filed on Sep. 21, 2009, now Pat. No. 7,816,503, which is a continuation of application No. 11/494,279, filed on Jul. 27, 2006, now Pat. No. 7,592,435.

(30) Foreign Application Priority Data

Aug. 19, 2005 (GB) .................................. 0517097.2

(51) Int. Cl.
- C07H 21/04 (2006.01)
- C07H 19/04 (2006.01)
- C12Q 1/68 (2006.01)
- C12P 19/34 (2006.01)
- B01L 3/00 (2006.01)

(52) U.S. Cl. .................. 536/23.1; 536/24.3; 536/24.33; 536/26.6; 435/6; 435/91.1; 422/430

(58) Field of Classification Search ................. 536/23.1, 536/24.3, 24.33, 26.6; 435/6, 91.1; 422/430
See application file for complete search history.

(56) References Cited

U.S. PATENT DOCUMENTS

| | | |
|---|---|---|
| 4,711,955 A | 12/1987 | Ward et al. |
| 4,772,691 A | 9/1988 | Herman |
| 4,824,775 A | 4/1989 | Dattagupta et al. |
| 4,863,849 A | 9/1989 | Melamede |
| 5,118,605 A | 6/1992 | Urdea |
| 5,174,962 A | 12/1992 | Brennan |
| 5,175,269 A | 12/1992 | Stavrianopoulos |
| 5,302,509 A | 4/1994 | Cheeseman |
| 5,328,824 A | 7/1994 | Ward et al. |
| 5,436,143 A | 7/1995 | Hyman |
| 5,449,767 A | 9/1995 | Ward et al. |
| 5,476,928 A | 12/1995 | Ward et al. |
| 5,516,664 A | 5/1996 | Hyman |

(Continued)

FOREIGN PATENT DOCUMENTS

DE 4141178 6/1993

(Continued)

OTHER PUBLICATIONS

Anonymous, "Gene Characterization Kits", p. 39, Stratagene Catalog (1988).

(Continued)

*Primary Examiner* — Jezia Riley
(74) *Attorney, Agent, or Firm* — Jones Day

(57) ABSTRACT

The invention is directed to modified guanine-containing nucleosides and nucleotides and uses thereof. More specifically, the invention relates to modified fluorescently labelled guanine-containing nucleosides and nucleotides which exhibit enhanced fluorophore intensity by virtue of reduced quenching effects.

19 Claims, 1 Drawing Sheet

U.S. PATENT DOCUMENTS

| | | |
|---|---|---|
| 5,534,424 A | 7/1996 | Uhlen |
| 5,547,839 A | 8/1996 | Dower et al. |
| 5,547,859 A | 8/1996 | Goodman et al. |
| 5,602,000 A | 2/1997 | Hyman |
| 5,763,594 A | 6/1998 | Hiatt et al. |
| 5,770,367 A | 6/1998 | Southern et al. |
| 5,798,210 A | 8/1998 | Canard et al. |
| 5,808,045 A | 9/1998 | Hiatt et al. |
| 5,821,356 A | 10/1998 | Khan et al. |
| 5,849,542 A | 12/1998 | Reeve et al. |
| 5,872,244 A | 2/1999 | Hiatt et al. |
| 5,885,775 A | 3/1999 | Haff et al. |
| 6,001,566 A | 12/1999 | Canard et al. |
| 6,008,379 A | 12/1999 | Benson et al. |
| 6,046,005 A | 4/2000 | Ju et al. |
| 6,074,823 A | 6/2000 | Koster |
| 6,087,095 A | 7/2000 | Rosenthal et al. |
| 6,136,543 A | 10/2000 | Anazawa et al. |
| 6,214,987 B1 | 4/2001 | Hiatt et al. |
| 6,218,118 B1 | 4/2001 | Sampson et al. |
| 6,218,530 B1 | 4/2001 | Rothschild et al. |
| 6,232,465 B1 | 5/2001 | Hiatt et al. |
| 6,242,193 B1 | 6/2001 | Anazawa et al. |
| 6,255,475 B1 | 7/2001 | Kwiatkowski |
| 6,287,821 B1 | 9/2001 | Shi et al. |
| 6,309,836 B1 | 10/2001 | Kwiatkowski |
| 6,312,893 B1 | 11/2001 | Van Ness et al. |
| 6,380,378 B1 | 4/2002 | Kitamura et al. |
| 6,524,829 B1 | 2/2003 | Seeger |
| 6,613,508 B1 | 9/2003 | Ness et al. |
| 6,613,523 B2 | 9/2003 | Fischer |
| 6,639,088 B2 | 10/2003 | Kwiatkowski |
| 6,664,079 B2 | 12/2003 | Ju et al. |
| 6,780,591 B2 | 8/2004 | Williams et al. |
| 6,787,308 B2 | 9/2004 | Balasubramanian et al. |
| 6,911,345 B2 | 6/2005 | Quake et al. |
| 6,982,146 B1 | 1/2006 | Schneider et al. |
| 7,037,654 B2 | 5/2006 | Chenna et al. |
| 7,037,687 B2 | 5/2006 | Williams et al. |
| 7,056,666 B2 | 6/2006 | Dower et al. |
| 7,057,026 B2 | 6/2006 | Barnes et al. |
| 7,057,031 B2 | 6/2006 | Olejnik et al. |
| 7,057,206 B2 | 6/2006 | Halik et al. |
| 7,074,597 B2 | 7/2006 | Ju |
| 7,078,499 B2 | 7/2006 | Odedra et al. |
| 7,105,300 B2 | 9/2006 | Parce et al. |
| 7,414,116 B2 | 8/2008 | Milton et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 7,771,973 B2 | 8/2010 | Milton et al. |
| 7,772,384 B2 | 8/2010 | Balasubramanian et al. |
| 7,785,796 B2 | 8/2010 | Balasubramanian et al. |
| 7,795,424 B2 | 9/2010 | Liu et al. |
| 7,816,503 B2 | 10/2010 | Milton et al. |
| 8,071,739 B2 | 12/2011 | Milton et al. |
| 8,084,590 B2 | 12/2011 | Milton et al. |
| 2003/0008285 A1 | 1/2003 | Fischer |
| 2003/0104437 A1 | 6/2003 | Barnes et al. |
| 2003/0186256 A1 | 10/2003 | Fischer |
| 2004/0014096 A1 | 1/2004 | Anderson et al. |
| 2004/0096825 A1 | 5/2004 | Chenna et al. |
| 2006/0160081 A1 | 7/2006 | Milton et al. |
| 2006/0188901 A1 | 8/2006 | Barnes et al. |
| 2010/0317531 A1 | 12/2010 | Balasubramanian et al. |
| 2011/0183327 A1 | 7/2011 | Balasubramanian et al. |

FOREIGN PATENT DOCUMENTS

| | | |
|---|---|---|
| EP | 0 992 511 | 4/2000 |
| EP | 1 182 267 | 2/2002 |
| EP | 1 291 354 | 3/2003 |
| EP | 0 808 320 | 4/2003 |
| EP | 1 730 307 | 12/2006 |
| EP | 1 337 541 | 3/2007 |
| EP | 1 218 391 | 4/2007 |
| EP | 1 790 736 | 5/2007 |
| WO | 89/09282 | 10/1989 |
| WO | 90/13666 | 11/1990 |
| WO | 91/06678 | 5/1991 |
| WO | 92/10587 | 6/1992 |
| WO | 93/05183 | 3/1993 |
| WO | 93/21340 | 10/1993 |
| WO | 94/14972 | 7/1994 |
| WO | 96/07669 | 3/1996 |
| WO | 96/23807 | 8/1996 |
| WO | 96/27025 | 9/1996 |
| WO | 98/30720 | 7/1998 |
| WO | 99/05315 | 2/1999 |
| WO | 99/57321 | 11/1999 |
| WO | 00/02895 | 1/2000 |
| WO | 00/06770 | 2/2000 |
| WO | 00/15844 | 3/2000 |
| WO | 00/18956 | 4/2000 |
| WO | 00/21974 | 4/2000 |
| WO | 00/50642 | 8/2000 |
| WO | 00/53805 | 9/2000 |
| WO | 00/53812 | 9/2000 |
| WO | 00/70073 | 11/2000 |
| WO | 01/16375 | 3/2001 |
| WO | 01/23610 | 4/2001 |
| WO | 01/25247 | 4/2001 |
| WO | 01/32930 | 5/2001 |
| WO | 01/57248 | 8/2001 |
| WO | 01/57249 | 8/2001 |
| WO | 01/92284 | 12/2001 |
| WO | 02/02813 | 1/2002 |
| WO | 02/22883 | 3/2002 |
| WO | 02/29003 | 4/2002 |
| WO | 02/072892 | 9/2002 |
| WO | 02/079519 | 10/2002 |
| WO | 02/088381 | 11/2002 |
| WO | 02/088382 | 11/2002 |
| WO | 03/002767 | 1/2003 |
| WO | 03/020968 | 3/2003 |
| WO | 03/048178 | 6/2003 |
| WO | 03/048387 | 6/2003 |
| WO | 03/085135 | 10/2003 |
| WO | 2004/007773 | 1/2004 |
| WO | 2004/018493 | 3/2004 |
| WO | 2004/018497 | 3/2004 |
| WO | 2005/084367 | 9/2005 |
| WO | 2006/097320 | 9/2006 |
| WO | 2007/015168 | 2/2007 |

OTHER PUBLICATIONS

Bergmann, et al., "Allyl as internucleotide protecting group in DNA synthesis to be cleaved off by ammonia", Tetrahedron NL vol. 51 No. 25, 1995, 6971-6976.

Brunckova, et al., "Intramolecular Hydrogen Atom Abstraction in Carbohydrates and Nucleosides: Inversion of an ****'", Tetrahedron Letters 35, 1994, 6619-6622.

Burgess, et al., "An approach to Photolabile, Fluorescent Protecting Groups", J Org. Chem, 62:5165-5168 (1997).

Buschmann, et al., "Spectroscopic Study and Evaluation of Red-Absorbing Fluorescent Dyes", Bioconjugate Chem. 14: 195-204 (2003).

Canard, et al., "Catalytic editing properties of DNA polymerases", Proc. Natil. Acad. Sci., vol. 92, 1995, 10859-10863.

Canard B. and, Sarfati R.S , "DNA polymerase fluorescent substrates with reversible 3'-tags", Gene, 1994, pp. 1-6, vol. 148.

Crespo-Hernandez, et al., "Part 1. Photochemical and Photophysical Studies of Guanine Derivatives: Intermediates Contributing to its Photodestruction Mechanism in Aqueous solution and the participation of the Electron Adduct,", Photochemistry and Photobiology, 71(5):534-543 (2000).

Green , "Protective groups in organic synthesis", John Wiley & Sons NY, 1999, 67-74 & 574-576.

Greene, et al., "Protective Groups in Organic Synthesis", John Wiley & Sons, New York, 1991.

Guibe, et al., "Allylic Protecting Groups adn their use in a complex environment part I: Allylic Protection of Alcohols", Tetrahedron NL vol. 53 No. 40, 1997, 13509-13556.

Guibe, et al., "Allylic Protecting Groups and their use in a complex environment part II: Allylic protecting groups and their removal through Catalytic Palladium pi-Allyl Methodology", Tetrahedron NL vol. 54 No. 13, 1998, 2967-3042.

Hayakawa, et al., "O-Allyl protection of guanine and thymine residues in oligodeoxyribonucleotides", J of Organometallic Chemistry, CH vol. 58, 1993, 5551-5555.

Henner, et al., "Enzyme Action at 3' Termini of Ionizing Radiation-induced DNA Strand Breaks", The Journal of Biologicial Chemistry: 258, 1983, 15198-15205.

Hovinen, Jari et al., "Synthesis of 3' . . . ", JCS Perkin Trans 1, 1994, 211-217.

Ikeda, et al., "A non-radioactive DNA Sequencing Method Using Biotinylated Dideoxynucleoside Triophospates and ΔTth DNA Polymerase", 2:225-227 (1995).

Kitamura, et al., "(P ( C6H5) 3) CpRu+-Catalyzed Deprotection of Allyl Caboxylic Esters", JOC, American Chemistry Society vol. 67 No. 14, 2002, 4975-4977.

Kloosterman, et al., "The Relative stability of Allyl Ether, Allyloxycarbonyl Ester and prop-2 Enylidene acetal protective groups toward iridium, rhodium and palladium catalysts", Tetrahedtron letters NL vol. 26 No. 41, 1985, 5045-5048.

Kocienski , "Protecting groups", Georg Tieme Verlag, Stuttgart, 1994, 61-68.

Kraevskii, et al., "Substrate Inhibitors of DNA Biosynthesis", Molecular Biology 21, 1987, 25-29.

Krecmerova, et al., "Synthesis of 5' -O-Phosphonomethyl Derivatives of Pyrimidine 2' - Deoxynucleosides", Coll Czech Chem comm No. 55, 1990, 2521-2536.

Kurata, et al., "Fluorescent quenching-based quantitative detection of specific DNA/RNA using a BODIPY ( (R) ) FL-labeled probe or primer", Nucleic Acids Research , GB vol. 29 No. 6, 2001, E34.

Kvam, et al., "Characterization of singlet oxygen-induced guanine residue damage after photochemical treatment of free nucleosides and DNA", Biochimica et Biophysica Acta., 1217: 9-15 (1994).

Li, et al., "A photocleavable fluorescent nucleotide for DNA sequencing and analysis,", Proc. Natl. Acad. Sci. 100:414-419 (2003).

Maier, et al., "Abstract", Nucleosides & Nucleotides vol. 14 (3-5), 1995, 961-965.

Maier, et al., "Synthesis and Properties of New Fluorescein—Labeled Oligonucleotides", Nucleosides & Nucleotides 14, 1995, 961-965.

Markiewicz, et al., "A new method of synthesis of fluorescently labelled oligonucleotides and their application in DNA sequencing", Nucleic Acids Research 25, 1997, 3672-3680.

Markiewicz, et al., "Abstract", Nucleic Acids Research vol. 25 (18), 1997, 3672-3680.

Marquez, et al., "Selective Fluorescence Quenching of 2,3-Diazabicyclo(2.2.2)oct-2-ene by Nucleotides", Organic Letters, 5:3911-3914 (2003).

Metzker , "Termination of DNA synthesis by novel 3'-modified-deoxyribonucleoside 5'-triphosphases", Nucleic Acids Research, vol. 22(20), 1994, 4259-4267.

Nazarenko, et al., "Effect of primary and secondary structure of oligodeoxyribonucleotides on the fluorescent properties of conjugated dyes", Nucleic Acids Research, 30:2089-2095 (2002).

Nishino, et al., "Efficient Deanilidation of Phosphoranilidates by the Use of Nitrites and Acetic/Anhydride", Heteroatom Chemistry vol. 2, 1991, 187-196.

Olejnik, et al., "Photocleavable biotin derivatives: A versatile approach for the isolation of biomolecules", Proc Natl. Acad. Sci. 92:7590-7594 (1995).

Quaedflieg, et al., "An Alternative Approach towards the Synthesis of (3'-5') methylene Acetal Linked Dinucleosides", Tetrahedron letters, 33:, 1992, 3081-3084.

Rasolonjatovo, et al., "6-N- (N-Methylanthranylamido)-4-Oxo-Hexanoic Acid : A New Fluorescent Protecting Group Applicable to a New DNA Sequencing Method", Nucleosides & Nucleotides, 17:2021-2025 (1998).

Sarfati, et al., "Synthesis of fluorescent derivatives of 3'-O-(6-aminohexanoyl)-pyrimidine nucleosides 5Â?-triphosphates that act as DNA polymerase substrates reversibly tagged at C-3'", JCS Perkin Trans, 1995, 1163-1171.

Torimura, et al., "Fluorescence-Quencing Phenomenon by Photoinduced Electron Transfer between a Fluorescent Dye and Nucleotide Base", Analytical Sciences, 17:155-160 (2001).

Veeneman, et al., "An efficient approach to the synthesis of thymidine derivatives containing phosphate-isosteric methylene acetal linkages", Tetrahedron vol. 47, 1991, 1547-1562.

Wada, et al., "2-(Azidomethyl)benzoyl as a new protecting group in nucleosides,", Tetrahedron Letters, 42, 2001, 1069-1072.

Welch, et al., "Syntheses of Nucleosides Designed for Combinatorial DNA Sequencing", Chemistry, European Journal, 5:951-960 (1999).

Yamashita, et al., "Studies of Antitumor Agents, VII. Antitumor Activities of O-Alkoxyalkyl Derivatives of 2' —Deoxy-5-trifluoromethyluridine", Chem Pharm Bull, 35, 1987, 2373-2381.

Zavgorodny, et al., "S,X-Acetals in Nucleoside Chemistry III. Synthesis of 2' and 3' O-Azidomethyl Derivatives of Ribonucleosides", Nucleosides, Nucleotides & Nucleic Acids 19, 2000, 1977-1991.

Gitten, U.S. Appl. No. 90/008,152, Filed Aug 3, 2006.

Gitten, U.S. Appl. No. 90/008,149, Filed Aug 3, 2006.

Oksman, et al., "Conformation of 3'-substituted 2', 3'-dideoxyribonucleosides in aqueous solution: nucleoside analogs with potential antiviral activity", Nucleosides & Nucleotides, 10(1-3), 1991, 567-568.

Oksman, et al., "Solution conformations and hydrolytic stability of 2'and 3'-substituted 2', 3'-dideoxyribonucleosides, including some potential inhibitors of human immunodeficiency virus", Journal of Physical Organic Chemistry, 5(22), 1992, 741-747.

Zavgorodny, et al., "1-Alkylthiaolkylation of Nucleoside Hydroxyl Functions and its synthetic applications", Tetrahedron Letters vol. 32 No. 51, 1991, 7593-7596.

U.S. Appl. No. 13/316,204, filed Dec. 9, 2011, Liu et al.

U.S. Appl. No. 13/281,275, filed Oct. 25, 2012, Milton et al.

Kamal et al., "A Mild and Rapid Regeneration of Alcohols from Their Allylic Ethers by Chlorotrimethylsilane/Sodium Iodide", Tetrahedron Letters, 40:317-372 (1999).

Rao, et al., "Four Color FRET Dye Nucleotide Terminators for DNA Sequencing", Nucleosides, Nucleotides, & Nucleic Acids, 20:673-676 (2001).

Seeger, "Single Molecule Fluorescence: High-Performance Molecular Diagnosis and Screening", Bioforum, Git Verlag, Darmstadt, DE, 21(4):179-185 (German text and English translation) (1998).

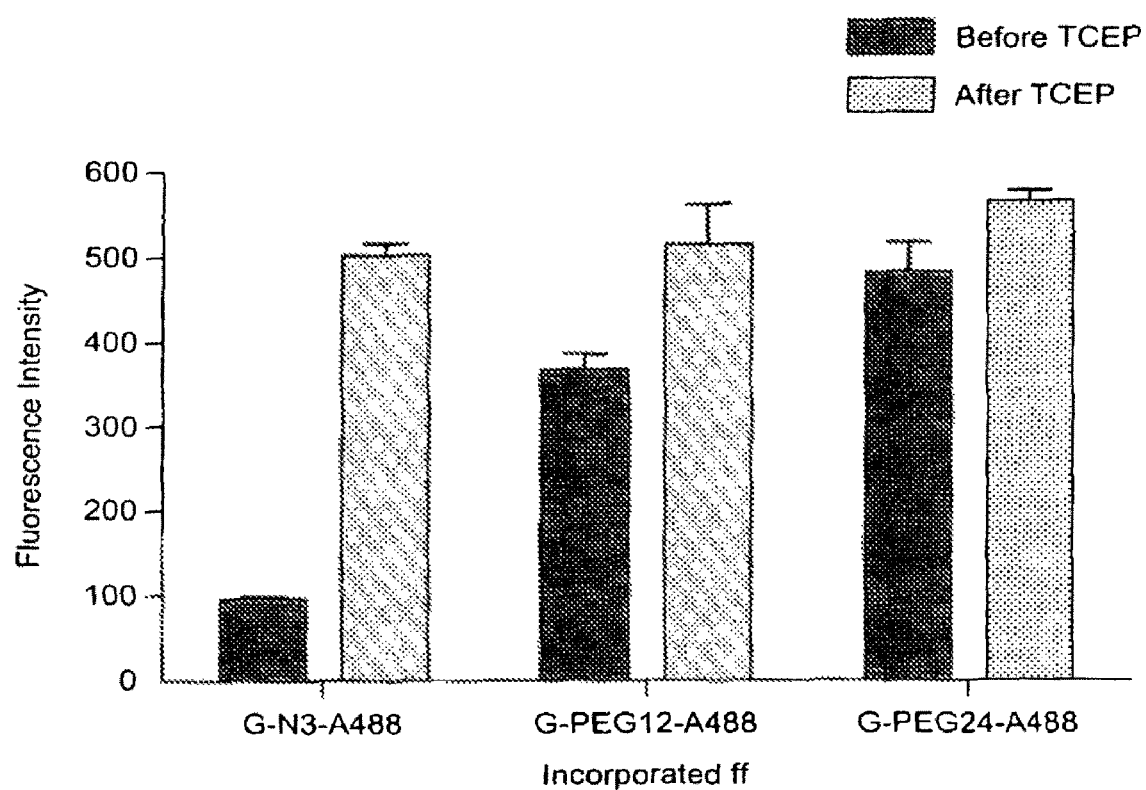

MODIFIED NUCLEOSIDES AND NUCLEOTIDES AND USES THEREOF

CROSS REFERENCE TO RELATED APPLICATIONS

The present application is a Continuation Application of U.S. application Ser. No. 12/586,385, filed on Sep. 21, 2009 (now U.S. Pat. No. 7,816,503), which is a Continuation Application of U.S. application Ser. No. 11/494,279, filed on Jul. 27, 2006 (now U.S. Pat. No. 7,592,435), which claims priority from Great Britain Application Serial No. 0517097.2, filed on Aug. 19, 2005. Applicants claim priority under 35 U.S.C. §120 as to the said United States applications and claim priority under 35 U.S.C. §119 as to the said Great Britain application. The entire disclosure of each application is incorporated herein by reference in their entireties.

FIELD OF THE INVENTION

The invention relates to modified guanine-containing nucleosides and nucleotides and more specifically to modified fluorescently labelled guanine-containing nucleosides and nucleotides which exhibit reduced quenching effects, and hence enhanced brightness of the fluorophore.

BACKGROUND TO THE INVENTION

Advances in the study of biological molecules have been led, in part, by improvement in technologies used to characterise the molecules or their biological reactions. In particular, the study of the nucleic acids DNA and RNA has benefited from developing technologies used for sequence analysis.

Nucleic acid sequencing methods have been known in the art for many years. One of the best-known methods is the Sanger "dideoxy" method which relies upon the use of dideoxyribonucleoside triphosphates as chain terminators. The Sanger method has been adapted for use in automated sequencing with the use of chain terminators incorporating fluorescent labels.

There are also known in the art methods of nucleic acid sequencing based on successive cycles of incorporation of fluorescently labelled nucleic acid analogues. In such "sequencing by synthesis" or "cycle sequencing" methods the identity of the added base is determined after each nucleotide addition by detecting the fluorescent label.

In particular, U.S. Pat. No. 5,302,509 describes a method for sequencing a polynucleotide template which involves performing multiple extension reactions using a DNA polymerase to successively incorporate labelled polynucleotides complementary to a template strand. In such a "sequencing by synthesis" reaction a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

The guanine base of DNA is known to act as a quencher of some fluorophores, meaning that a fluorophore attached to G is harder to detect than the equivalent fluorophore attached to C, A or T (Torimura et al., Analytical Sciences, 17: 155-160 (2001); Kurata at al., Nucleic Acids Res., 29(6) e34 (2001)). In the context of a sequencing reaction based on detection of fluorescent labelled nucleotides, this in turn means that the fluorescent signal detected from labelled guanine nucleotides incorporated during the sequencing reaction will be of lower intensity than that detected from labelled nucleotides bearing the same fluorophore attached to adenine, thymine or cytosine containing nucleotides. Thus, in certain circumstances the presence of a "G" nucleotide may be harder to call with certainty than the presence of A, T or C under the same reaction and detection conditions.

Accordingly, in the context of nucleic acid sequencing reactions it would be desirable to be able to increase the intensity of the fluorescent signal from fluorescently labelled G nucleotides so that the intensity of the signal compares more favourably with that which can be obtained from fluorescently labelled A, T or C nucleotides under the same reaction and detection conditions.

SUMMARY OF THE INVENTION

The inventors have now determined that by altering, and in particular increasing, the length of the linker between the fluorophore and the guanine base, so as to introduce a polyethylene glycol spacer group, it is possible to increase the fluorescence intensity compared to the same fluorophore attached to the guanine base through prior art linkages. The design of the linkers, and especially their increased length, also allows improvements in the brightness of fluorophores attached to the guanine bases of guanosine nucleotides when incorporated into polynucleotides such as DNA. The nucleotides of the invention are thus of use in any method of analysis which requires detection of a fluorescent label attached to a guanine-containing nucleotide, including but not limited to nucleic acid sequencing and nucleic acid labelling.

Therefore, in a first aspect invention provides a modified nucleotide or nucleoside comprising a guanine base or a derivative thereof attached to a fluorophore through a linking group, characterised in that said linking group comprises a spacer group of formula $-((CH_2)_2O)_n-$ wherein n is an integer between 2 and 50.

In a second aspect the invention provides a polynucleotide comprising at least one modified nucleotide according to the first aspect of the invention.

In a third aspect the invention provides use of a modified nucleotide or nucleoside according to the first aspect of the invention or a polynucleotide according to the second aspect of the invention in any method of analysis which requires detection of a fluorescent signal from the modified nucleotide or nucleoside.

In particular embodiments the invention provides use of a modified nucleotide or nucleoside according to the first aspect of the invention or a polynucleotide according to the second aspect of the invention in a method of nucleic acid sequencing, re-sequencing, whole genome sequencing, single nucleotide polymorphism scoring, or any other application involving the detection of the modified nucleotide or nucleoside when incorporated into a polynucleotide.

In a further aspect the invention provides a method of detecting a modified guanosine nucleotide incorporated into a polynucleotide which comprises:
(a) incorporating at least one modified nucleotide according to the first aspect of the invention into a polynucleotide and
(b) detecting the modified nucleotide(s) incorporated into the polynucleotide by detecting the fluorescent signal from said modified nucleotide(s).

In a preferred embodiment the at least one modified nucleotide is incorporated into a polynucleotide by the action of a polymerase enzyme.

In a particular embodiment step (a) may comprise incubating a template polynucleotide strand with a reaction mixture comprising fluorescently labelled modified nucleotides according to the first aspect of the invention and a polymerase under conditions which permit formation of a phosphodiester linkage between a free 3' hydroxyl group on a polynucleotide strand annealed to said template polynucleotide strand and a 5' phosphate group on said modified nucleotide.

Specific but non-limiting embodiments of this method comprise incorporation of modified nucleotides according to the invention by inter alia polymerase chain reaction (PCR), primer extension, nick translation or strand displacement polymerisation.

In a still further aspect, the invention provides a method of sequencing a template nucleic acid molecule comprising:

incorporating one or more nucleotides into a strand of nucleic acid complementary to the template nucleic acid and determining the identity of the base present in one or more incorporated nucleotide(s) in order to determine the sequence of the template nucleic acid molecule;

wherein the identity of the base present in said nucleotide(s) is determined by detecting a fluorescent signal produced by said nucleotide(s);

characterised in that at, least one incorporated nucleotide is a modified nucleotide according to the first aspect of the invention.

In a still further aspect, the invention provides a kit comprising a plurality of different nucleotides including a modified nucleotide according to the first aspect of this invention.

DESCRIPTION OF THE DRAWINGS

FIG. 1 shows a graph evidencing the improved brightness of the Alexa 488 fluorophore in modified nucleotides of the invention having —$((CH_2)_2O)_{11}$— (denoted G-PEG12-A488) and —$((CH_2)_2O)_{23}$— (denoted G-PEG24-A488) spacing groups over a modified nucleotide not of this invention with no such spacer (denoted G-$N_3$-A488, and improved brightness of the fluorophore having the —$((CH_2)_2O)_{23}$—, as opposed to the —$((CH_2)_2O)_{11}$—, spacing group. Fluorescence intensity was measured for each labelled nucleotide in 100 mM Tris, 30 mM NaCl pH7 when incorporated into polynucleotide both before and after treatment with TCEP to cleave the linking group. Cleavage of the linkers with TCEP shows that the free fluorophore is not quenched in solution, thus the enhanced signal is not simply caused by the PEG moiety attached to the fluorophore.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

When describing the invention, certain terms used have particular meanings to those skilled in the art some of which are as set forth below. These definitions are to be used in construing the terms unless the context dictates otherwise.

The invention, as described and claimed herein, provides improved modified guanosine nucleosides and nucleotides, methods of using these, particularly methods of using guanosine nucleotides in molecular biological applications where it is desired to monitor incorporation of the modified nucleotides into polynucleotides, including but not limited to sequencing by synthesis applications and other applications involving labelling of nucleic acids, and kits comprising such nucleosides or nucleotides.

As is known in the art, a "nucleotide" consists of a nitrogenous base, a sugar, and one or more phosphate groups. "Nucleosides" consist of the nitrogenous base and sugar only. In naturally occurring or native nucleotides the sugar component is usually either ribose, as in ribonucleotides and the corresponding polynucleotide RNA, or deoxyribose, i.e., a sugar lacking the 2' hydroxyl group that is present in ribose, as in deoxyribonucleotides and the corresponding polynucleotide DNA. The naturally occurring sugars may be modified, for example by removal or substitution of the 3' hydroxyl group. The nitrogenous base is a derivative of purine or pyrimidine. The purines are adenine (A) and guanine (G), and the pyrimidines are cytosine (C) and thymine (T) (or in the context of RNA, uracil (U)). The equivalent nucleosides incorporating these bases are respectively denoted adenosine, guanosine, cytidine and thymidine. The C-1 atom of deoxyribose is bonded to N-1 of a pyrimidine or N-9 of a purine. A nucleotide is also a phosphate ester of a nucleoside, with esterification occurring on the hydroxyl group attached to C-5 of the sugar. Nucleotides may be mono, di, tri or cyclic phosphates.

The modified nucleotides or nucleosides of the invention comprise the guanine base, sugar (and one or more phosphate groups, if appropriate) and a detectable label comprising a fluorophore. The detectable label is attached to the guanine base through a linking group.

In the modified nucleosides and nucleotides of the invention the linking group comprises a polyethylene glycol spacer, although other suitably hydrophilic groups of similar length to the polyethylene glycol spacers of the invention (approximately 5 to 150 atoms) may be used as an alternative to polyethylene glycol spacers. Preferably the spacer comprises between 5 and 30 ethylene oxide groups —$(CH_2)_2O)$—, still more preferably between 10 and 25 ethylene oxide groups. Exemplified herein, and thus particularly preferred ethylene oxide spacer groups are —$((CH_2)_2O)_{11}$— and —$((CH_2)_2O)_{23}$—, preferably —$((CH_2)_2O)_{23}$—.

The linking groups used in the present invention serve to space the fluorescent label away from the guanine base such that the amount of quenching of the fluorescent signal from the fluorophore by the guanine base is reduced or substantially eliminated, as compared to a nucleotide or nucleoside of analogous structure but lacking the linking group. At the same time, the fluorophore is maintained in indirect covalent attachment with the remainder of the nucleotide/nucleoside.

The nature of the fluorophore present in the fluorescent label is generally not limited. It may be any fluorophore compatible with labelling of nucleosides/nucleotides and, depending on the intended use of the modified nucleotides, also with subsequent incorporation of the modified nucleotides into a polynucleotide. The invention is particularly applicable to modified nucleotides labelled with any fluorophore that shows a decrease in the fluorescence emission intensity when covalently attached to a guanosine nucleotide. Appropriate fluorophores are well known to those skilled in the art and may be obtained from a number of commercial manufacturers, such as Molecular Probes Inc.

For example, Welch et al. (*Chem. Hun. J.* 5(3):951-960, 1999) discloses dansyl-functionalised fluorescent moieties that can be used in the present invention. Zhu et al., (*Cytometry* 28:206-211, 1997) describes the use of the fluorescent labels Cy3 and Cy5, which can also be used in, the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11):4593-4602, 1987) and Smith et al., (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

For example, two classes of particularly preferred fluorophores which may be used according to this invention are the Alexa series available from Molecular Probes, (sometimes referred to as Alexa Fluor dyes) and fluorescent labels in the Atto series available from Atto-tec (sometimes referred to as Atto fluorescent labels) of Atto-tec. An example of a preferred Alexa dye is Alexa 488, and an example of a particular Atto dye is Atto 532.

Other than the ethylene oxide spacer moiety, the linkage between the base and detectable label may comprise other chemical functionality. This may serve to afford cleavable or non-cleavable linkers. Examples of cleavable linkers are known to those skilled in the art (see for example Applicant's published International patent applications WO03/048387 and WO2004/018493).

As aforesaid, the sugar components of the nucleosides and nucleotides according to the invention may be further modified (from the native ribose or deoxyribose) in order to confer some useful property without affecting the function of the fluorescent label component. A particularly preferred embodiment of the invention is the provision of modified guanosine nucleosides and nucleotides having a cleavable 3' blocking group, and most preferably deoxyribonucleosides and deoxyribonucleotides including such a 3' blocking group. Exemplary, and preferred, blocking groups are described in our co-pending application WO 2004/018497. Preferably the nucleoside and nucleotides of the invention contain a 3' blocking group and a cleavable linker to the detectable label, more preferably still wherein the block and linker may both be cleaved under the same conditions so as to reveal the 3'-OH group in the resultant product upon a single chemical reaction. Examples of such functionalities are described fully in WO2004/018497.

Linkage of the fluorescent label to the guanine base via the linking group may be to any suitable position of the base, provided that it does not interfere with the intended function/use of the modified nucleotide or nucleoside. For example, if a modified nucleotide according to the invention is to be enzymatically incorporated into a polynucleotide by the action of a polymerase then the position of linkage of the fluorescent label via the linking group should not prevent such enzymatic incorporation. Typically linkage will be via the 7 position of the "guanine" base. It will be appreciated that in order to provide the necessary valency for covalent linkage at the 7 position a 7-deaza guanine derivative may be used in preference to the native guanine base. Accordingly, references herein to modified "guanine-containing" nucleosides or nucleotides or to modified "guanosine" nucleosides or nucleotides should be interpreted as encompassing analogous structures which contain a guanine derivative, and in particular 7-deaza guanine, rather than the native guanine base, unless the context implies otherwise. In other embodiments the linking group may be attached to the 8 position of the guanine ring system. Further modifications or substitutions may be included elsewhere in the guanine ring system, in addition to the position at which the linking group is attached, as in for example 7-deaza-8-aza guanine. Again references herein to modified "guanine-containing" nucleosides or nucleotides or to modified "guanosine" nucleosides or nucleotides should be interpreted as encompassing such further modified forms of the guanine base unless the context implies otherwise.

In specific, but non-limiting, embodiments described herein with reference to the accompanying examples the invention provides:

7-[3-(-Alexa488-PEG$_{12}$-LN$_3$-linker acetylamino)-prop-1-ynyl]-3'-azidomethyl-dGTP, and 7-[3-(-Alexa488-PEG$_{24}$-LN$_3$-linker acetylamino)-prop-1-ynyl]-3'-azidomethyl-dGTP The invention also encompasses polynucleotides incorporating one or more modified guanosine nucleotides according to the invention. Preferably such polynucleotides will be DNA or RNA, comprised respectively of deoxyribonucleotides or ribonucleotides joined in phosphodiester linkage. Polynucleotides according to the invention may comprise naturally occurring nucleotides, non-natural (or modified) nucleotides other than the modified nucleotides of the invention or any combination thereof, provided that at least one modified nucleotide according to the invention is present. Polynucleotides according to the invention may also include non-natural backbone linkages and/or non-nucleotide chemical modifications. Chimeric structures comprised of mixtures of ribonucleotides and deoxyribonucleotides are also contemplated Preferred Uses of the Nucleotides of the Invention The modified nucleotides (or nucleosides) of the invention may be used in any method of analysis which requires detection of a fluorescent label attached to a guanine-containing nucleotide or nucleoside, whether on its own or incorporated into or associated with a larger molecular structure or conjugate. In all such methods of analysis the use of the modified guanosine nucleotides or nucleosides of the invention provides an advantage in that the brightness of the fluorescent signal is increased compared to that which would be obtained using guanosine nucleotides or nucleosides of analogous structure but lacking the longer linking group present in the modified nucleotides or nucleosides of the invention.

In particular embodiments of the invention, modified nucleotides of the invention may be used in any method of analysis which requires detection of a fluorescent label attached to a modified guanine nucleotide incorporated into a polynucleotide. In this context the term "incorporated into a polynucleotide" requires that the 5' phosphate is joined in phosphodiester linkage to the 3' hydroxyl group of a second (modified or unmodified) nucleotide, which may itself form part of a longer polynucleotide chain. The 3' end of the modified nucleotide of the invention may or may not be joined in phosphodiester linkage to the 5' phosphate of a further (modified or unmodified) nucleotide.

Thus, in one non-limiting embodiment the invention provides a method of detecting a modified guanosine nucleotide incorporated into a polynucleotide which comprises:

(a) incorporating at least one modified nucleotide according to the first aspect of the invention into a polynucleotide and (b) detecting the modified nucleotide(s) incorporated into the polynucleotide by detecting the fluorescent signal from said modified nucleotide(s).

This method requires two essential steps: a synthetic step (a) in which one or more modified nucleotides according to the invention are incorporated into a polynucleotide and a detection step (b) in which one or more modified nucleotide(s) incorporated into the polynucleotide are detected by detecting or quantitatively measuring their fluorescence.

In a preferred embodiment the at least one modified nucleotide is incorporated into a polynucleotide in the synthetic step by the action of a polymerase enzyme. However, other methods of joining modified nucleotides to polynucleotides, such as for example chemical oligonucleotide synthesis, are not excluded. Therefore, in the specific context of this method of the invention, the term "incorporating" a nucleotide into a polynucleotide encompasses polynucleotide synthesis by chemical methods as well as enzymatic methods.

In a specific embodiment the synthetic step may comprise incubating a template polynucleotide strand with a reaction mixture comprising fluorescently labelled modified guanosine nucleotides of the invention and a polymerase under conditions which permit formation of a phosphodiester linkage between a free 3' hydroxyl group on a polynucleotide strand annealed to said template polynucleotide strand and a 5' phosphate group on said modified nucleotide.

This embodiment comprises a synthetic step in which formation of a polynucleotide strand is directed by complementary base-pairing of nucleotides to a template strand.

In all embodiments of the method, the detection step may be carried out whilst the polynucleotide strand into which the modified guanosine nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the modified nucleotide(s) may be isolated or purified and then processed further or used in a subsequent analysis. By way of example, target polynucleotides labelled with modified nucleotide(s) according to the invention in a synthetic step may be subsequently used as labelled probes or primers. In other embodiments the product of the synthetic step (a) may be subject to further reaction steps and, if desired, the product of these subsequent steps purified or isolated.

Suitable conditions for the synthetic step will be well known to those familiar with standard molecular biology techniques. In one embodiment the synthetic step may be analogous to a standard primer extension reaction using nucleotide precursors, including modified guanosine nucleotides according to the invention, to form an extended target strand complementary to the template strand in the presence of a suitable polymerase enzyme. In other embodiments the synthetic step may itself form part of a polymerase chain reaction producing a labelled double-stranded PCR product comprised of annealed complementary strands derived from copying of the target and template polynucleotide strands. Other exemplary "synthetic" steps include nick translation, strand displacement polymerisation, random primed DNA labelling etc.

The polymerase enzyme used in the synthetic step must be capable of catalysing the incorporation of modified guanosine nucleotides according to the invention. Otherwise, the precise nature of the polymerase is not particularly limited but may depend upon the conditions of the synthetic reaction. For example, if the synthetic reaction is a PCR reaction then a thermostable polymerase is required, whereas this is not essential for standard primer extension. Suitable thermostable polymerases which are capable of incorporating the modified nucleotides according to the invention include those described in WO 2005/024010.

In specific non-limiting embodiments the invention encompasses use of the modified nucleotides or nucleosides according to the invention in a method of nucleic acid sequencing, re-sequencing, whole genome sequencing, single nucleotide polymorphism scoring, any other application involving the detection of the modified nucleotide or nucleotide when incorporated into a polynucleotide, or any other application requiring the use of polynucleotides labelled with the fluorescent modified nucleotides according to the invention.

In a particularly preferred embodiment the invention provides use of modified nucleotides according to the invention in a polynucleotide "sequencing-by-synthesis" reaction. Sequencing-by-synthesis generally involves sequential addition of one or more nucleotides to a growing polynucleotide chain in the 5' to 3' direction using a polymerase in order to form an extended polynucleotide chain complementary to the template nucleic acid, to be sequenced. The identity of the base present in one or more of the added nucleotide(s) is determined in a detection or "imaging" step. The identity of the added base is preferably determined after each nucleotide incorporation step. The sequence of the template may then be inferred using conventional Watson-Crick base-pairing rules. For the avoidance of doubt "sequencing" can also encompass incorporation and identification of a single nucleotide. Determination of the identity of a single base may be useful, for example, in the scoring of single nucleotide polymorphisms.

In nucleic acid sequencing protocols, because the brightness of the fluorescent signal obtained from the modified nucleotides of the invention is increased compared to that which would be obtained using guanosine nucleotides of analogous structure but lacking the longer linking group present in the modified nucleotides or nucleosides of the invention, it is possible to "call" the presence of G nucleotides accurately at much lower template concentrations. With prior art guanosine nucleotides the brightness of the fluorescence from G may be a limiting factor on the performance of any given sequencing reaction, particularly affecting the lower limit on the amount of template which must be added to the reaction. With the use of the modified nucleotides of the invention the amount of fluorescence from each individual incorporated guanosine nucleotide is increased, hence it may be possible to accurately sequence reduced amounts of template.

In an embodiment of the invention, the sequence of a template polynucleotide is determined in a similar manner to that described in U.S. Pat. No. 5,654,413, by detecting the incorporation of one or more nucleotides into a nascent strand complementary to the template polynucleotide to be sequenced through the detection of fluorescent label(s) attached to the incorporated nucleotide(s). Sequencing of the template polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalysed reaction.

In preferred embodiments each of the different nucleotides (A, T, G and C) is labelled with a unique fluorophore which acts as a blocking group at the 3' position to prevent uncontrolled polymerisation. The polymerase enzyme incorporates a nucleotide into the nascent chain complementary to the template polynucleotide, and the blocking group prevents further incorporation of nucleotides. Any unincorporated nucleotides are removed and each incorporated nucleotide is "read" optically by suitable means, such as a charge-coupled device using laser excitation and filters. The 3'-blocking group is then removed (deprotected), to expose the nascent chain for further nucleotide incorporation. Typically the identity of the incorporated nucleotide will be determined after each incorporation step but this is not strictly essential.

Similarly, U.S. Pat. No. 5,302,509 discloses a method to sequence polynucleotides immobilised on a solid support. The method relies on the incorporation of fluorescently-labelled, 3'-blocked nucleotides A, G, C and T into a growing strand complementary to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

The nucleic acid, template to be sequenced in a sequencing-by-synthesis reaction may be any polynucleotide that it is desired to sequence. The nucleic acid template for a sequencing reaction will typically comprise a double-stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridises to a single-stranded region of the template to be sequenced. Alternatively, the primer and the template strand to be sequenced may each form part of a partially self-complementary nucleic acid strand capable of forming an intramolecular duplex, such as for example a hairpin loop structure. Preferred hairpin polynucleotides and methods by which they may be attached to solid supports are disclosed in our co-pending International application publication no. WO 2005/047301.

Nucleotides are added successively to the free 3' hydroxyl group, resulting in synthesis of a polynucleotide chain in the 5' to 3' direction. The nature of the base which has been added may be determined, preferably but not necessarily after each nucleotide addition, thus providing sequence information for the nucleic acid template.

The term "incorporation" of a nucleotide into a nucleic acid strand (or polynucleotide) refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art. Preferably linkage will be via covalent attachment.

In certain embodiments template polynucleotides may be attached directly to a solid support (e.g. a silica-based support). However, in other embodiments of the invention the surface of the solid support may be modified in some way so as to allow either direct covalent attachment of template polynucleotides, or to immobilise the template polynucleotides through a hydrogel or polyelectrolyte multilayer, which may itself be non-covalently attached to the solid support.

Arrays in which polynucleotides have been directly attached to silica-based supports are those for example disclosed in WO 97/04131, wherein polynucleotides are immobilised on a glass support by reaction between a pendant epoxide group on the glass with an internal amino group on the polynucleotide. In addition, we disclose in our co-pending International patent application publication number WO2005/047301 arrays of polynucleotides attached to a solid support, e.g. for use in the preparation of SMAs, or clustered microarrays, by reaction of a sulfur-based nucleophile with the solid support.

A still further example of solid-supported template polynucleotides is where the template polynucleotides are attached a to hydrogel supported upon silica-based or other solid supports. Silica-based supports are typically used to support hydrogels and hydrogel arrays as described in WO00/31148, WO01/01143, WO02/12566, WO03/014392, U.S. Pat. No. 6,465,178 and WO00/53812.

A particularly preferred surface to which template polynucleotides may be immobilised is a polyacrylamide hydrogel. Polyacrylamide hydrogels are described in the prior art, some of which is discussed above. However, a particularly preferred hydrogel is described in WO 2005/065814.

Preferably, where the template polynucleotide is immobilized on or to a solid support, this comprises a planar wave guide as is described in our co-pending British patent application no. 0507835.7.

The use of a planar wave guide serves to enhance the sensitivity of detection of a nucleotide incorporated into a polynucleotide molecule, wherein the incorporated nucleotide is detected by detecting a signal produced by said nucleotide when exposed to an evanescent field generated by coupling of light into said planar waveguide.

The template(s) to be sequenced may form part of an "array" on a solid support, in which case the array may take any convenient form. Thus, the method of the invention is applicable to all types of "high density" arrays, including single-molecule arrays and clustered arrays.

The method of the invention may be used for sequencing templates on essentially any type of array formed by immobilisation of nucleic acid molecules on a solid support, and more particularly any type of high-density array. However, the method of the invention is particularly advantageous in the context of sequencing of clustered arrays.

In multi-polynucleotide or clustered arrays distinct regions on the array comprise multiple polynucleotide template molecules. The term "clustered array" refers to an array wherein distinct regions or sites on the array comprise multiple polynucleotide molecules that are not individually resolvable by optical means. Depending on how the array is formed each site on the array may comprise multiple copies of one individual polynucleotide molecule or even multiple copies of a small number of different polynucleotide molecules (e.g. multiple copies of two complementary nucleic acid strands).

Multi-polynucleotide or clustered arrays of nucleic acid molecules may be produced using techniques generally known in the art. By way of example, WO 98/44151 and WO 00/18957 both describe methods of nucleic acid amplification which allow amplification products to be immobilised on a solid support in order to form arrays comprised of clusters or "colonies" of immobilised nucleic acid molecules. The nucleic acid molecules present on the clustered arrays prepared according to these methods are suitable templates for sequencing using the method of the invention.

The sequencing method of the invention is also applicable to sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to effect individual resolution of the polynucleotides. The target nucleic acid molecules immobilised onto the surface of the solid support should thus be capable of being resolved by optical means. This means that, within the resolvable area of the particular imaging device used, there must be one or more distinct signals, each representing one polynucleotide. This may be achieved, preferably wherein the spacing between adjacent polynucleotide molecules on the array is at least 100 nm, more preferably at least 250 nm, still more preferably at least 300 nm, even more preferably at least 350 nm. Thus, each molecule is individually resolvable and detectable as a single molecule fluorescent point, and fluorescence from said single molecule fluorescent point also exhibits single step photobleaching. The terms "individually resolved" and "individual resolution" are used herein to specify that, when visualised, it is possible to distinguish one molecule on the array from its neighbouring molecules. Separation between individual molecules on the array will be determined, in part, by the particular technique used to resolve the individual molecules. The general features of single molecule arrays will be understood by reference to published applications WO 00/60770 and WO 01/57248.

Although a preferred use of the modified nucleotides of the invention is in sequencing-by-synthesis reactions the utility of the modified nucleotides is not limited to such methods. In fact, the nucleotides may be used advantageously in any sequencing methodology which requires detection of fluorescent labels attached to guanosine nucleotides incorporated into a polynucleotide.

In particular, the modified nucleotides of the invention may be used an automated fluorescent sequencing protocols, particularly fluorescent dye-terminator cycle sequencing based on the chain termination sequencing method of Sanger and co-workers. Such methods generally use PCR to incorporate fluorescently labelled dideoxynucleotides in a primer extension sequencing reaction.

So-called Sanger sequencing methods, and related protocols (Sanger-type), rely upon randomised chain-termination at labeled dideoxynucleotides including a known base. An example of a Sanger-type sequencing protocol is the BASS method described by Metzker (*Nucleic Acids Research*, 22(2)):4259-4267, 1994). Other Sanger-type sequencing methods will be known to those skilled in the art.

Thus, the invention also encompasses modified guanosine nucleotides according to the invention which are dideoxynucleotides lacking hydroxyl groups at both the 3' and 2' positions, such modified dideoxynucleotides being suitable for use in Sanger type sequencing methods. Modified guanosine nucleotides of the present invention incorporating 3' blocking groups, it will be recognized, may also be of utility in Sanger methods and related protocols since the same effect achieved by using modified dideoxyguanosine nucleotides may be achieved by using guanosine nucleotides having 3'-OH blocking groups: both prevent incorporation of subsequent nucleotides.

Where nucleotides according to the present invention, and having a 3' blocking group are to be used in Sanger or a Sanger-type sequencing methods it will be appreciated that the detectable labels attached to the nucleotides need not be connected via cleavable linkers, since in each instance where a labeled nucleotide of the invention is incorporated, no nucleotides need to be subsequently incorporated and thus the label need not be removed from the nucleotide.

The invention also provides kits including modified guanosine nucleosides and/or nucleotides according to the invention. Such kits will generally include a supply of at least one modified nucleotide or nucleoside according to the invention together with at least one further component. The further component(s) may be further modified or unmodified nucleotides or nucleosides. For example, modified guanosine nucleotides according to the invention may be supplied in combination with unlabelled or native guanosine nucleotides, and/or with unlabelled or native adenosine, cytidine or thymidine nucleotides and/or with fluorescently labeled adenosine, cytidine or thymidine nucleotides or any combination thereof. Combinations of nucleotides may be provided as separate individual components or as nucleotide mixtures In other embodiments the kits may include a supply of a polymerase enzyme capable of catalyzing incorporation of the modified guanosine nucleotides into a polynucleotide. The polymerase component may be included in addition to or instead of further nucleotide components. Other components to be included in such kits may include buffers etc.

The modified nucleotides according to the invention, and other any nucleotide components including mixtures of different nucleotides, may be provided in the kit in a concentrated form to be diluted prior to use. In such embodiments a supply of a suitable dilution buffer may be included.

The invention will be further understood with reference to the following experimental examples.

EXAMPLES

Example 1

Synthesis of 7-[3-(-Alexa488-PEG$_{12}$-LN$_3$-linker acetylamino)-prop-1-ynyl]-3'-azidomethyl-dGTP (3)

Alexa488-PEG$_{12}$ carboxylic acid (1)

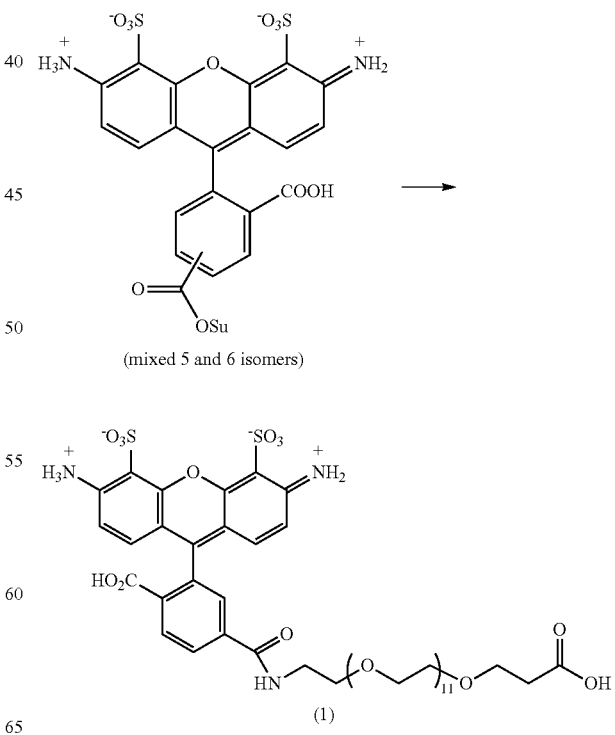

(mixed 5 and 6 isomers)

(1)

Alexa fluor 488 carboxylic acid succinimidyl ester (mixed isomers, 20 mg, 31 μmoles) was dissolved in dry DMF (1 ml). A solution of amino dPEG$_{12}$ acid (55.5 mg, 90 μmoles) and DIPEA (31.3 μl, 180 μmoles) in 0.1 M triethyl ammonium bicarbonate buffer (TEAB, 0.5 ml, pH 7.5) was added. The reaction was then stirred at RT for 3 hrs. All the reaction mixture was diluted with 0.1 M TEAB (5 ml) and loaded onto a column of DEAE-A25 Sephadex (1×12 cm). The column was eluted with 0.1 M (60 ml), 0.3 M (80 ml) (product fractions) and 0.6 M (80 ml) (fraction of free carboxylic acid form of Alexa fluor 488) TEAB. 0.1 M eluent was discarded. 0.3 M eluent was collected and evaporated under reduced pressure. The residue was co-evaporated with water (2×10 ml) and then further purified by semi preparative reverse phase HPLC [HPLC gradient: A, 100% 0.1 M TEAB; B 100% MeCN; 0-2 min, 2% B (flow 2-5 ml/min); 2-20 min, 2-20% B (flow 5 ml/min); 20-22 min, 20-95% B (flow 5 ml/min); 22-25 min, 95% B (flow 5 ml/min); 25-27 min, 95-2% B (flow 5 ml/min); 27-30 min, 2% B (flow 5-2 ml/min)]. The first isomer product with retention time of 19.11 min was collected and evaporated under reduced pressure and the residue was co-evaporated with water (2×5 ml) to give the title compound as triethyl ammonium salt (5.22 μmol, quantification at $\lambda_{max(493)}$ in 0.1 M TEAB buffer, 16.8%). This isomer was used to forward synthesis. The second isomer product with retention time 19.73 min was kept aside. $^1$HNMR of product with Rt 19.11 min in D$_2$O indicated approximately two triethylammonium count ions. $^1$H NMR (400 MHz, D$_2$O), δ 1.11 (t, J=7.3 Hz, 18H, CH$_3$, triethylammonium count ion), 2.37 (t, J=6.4 Hz, 2H, CH$_2$), 3.03 (q, J=7.3 Hz, 12H, CH$_2$, triethylammonium count ion), 3.30-3.70 (m, 50H), 6.80 (d, J=9.3 Hz, 2H, Ar—H), 7.08 (d, J=9.3 Hz, 2H, Ar—H), 7.53 (s, 1H, Ar—H) and 7.80-7.95 (m, 2H, Ar—H). LC-MS (electrospray negative): 565.85 [(M/2e)−1].

Alexa488-PEG$_{12}$-LN$_3$ linker carboxylic acid (2)

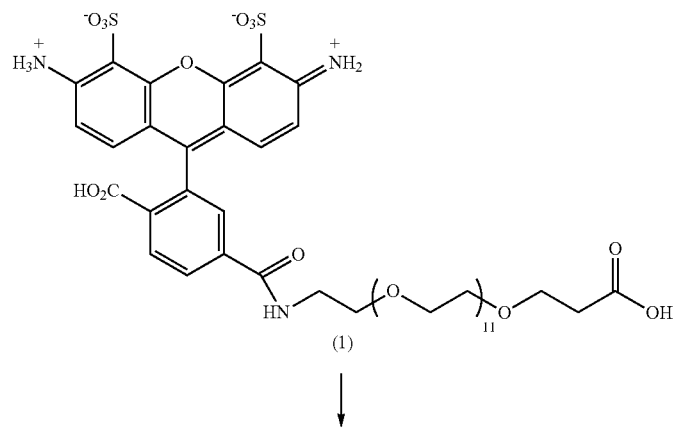

(1)

↓

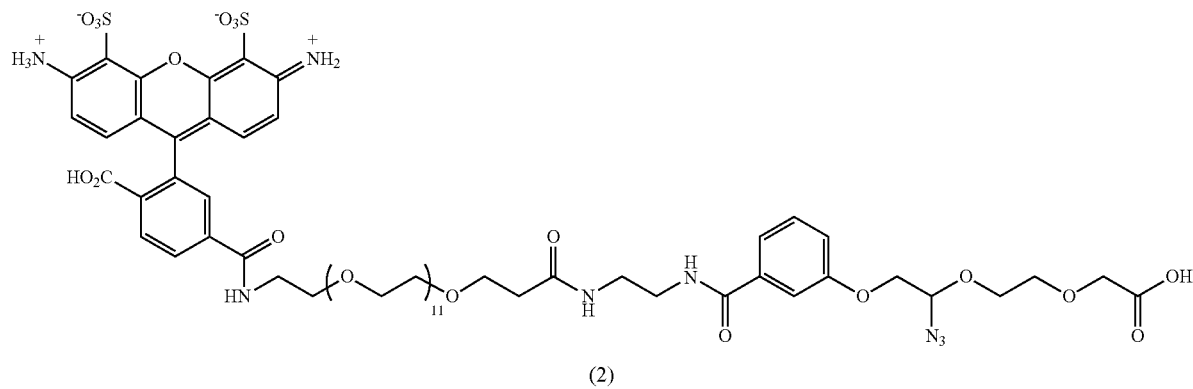

(2)

Alexa488-PEG$_{12}$ carboxylic acid (1) (5 μmol) was co-evaporated with dry DMF (5 ml) and the residue was then dissolved in dry DMF (1.5 ml). A solution of TSTU (10 μmol, 100 μl, concentration: 30 mg TSTU in 1 ml dry DMF) in dry DMF was added. The reaction was stirred at room temperature for 10 minutes. LN$_3$ linker ((2-{2-[3-(2-amino-ethylcarbamoyl)-phenoxy]-1-azido-ethoxy}-ethoxy)-acetic acid) (15 μmol, 5.51 mg) was added followed by DIPEA (50 μmol, 8.7 μl). The reaction was stirred at room temperature overnight. The reaction was then diluted with 0.1 M TEAB buffer (10 ml) and then loaded onto a DEAE-A25 Sephadex column (1×10 cm). The column was eluted with 0.1 M TEAB (60 ml, this fraction was discarded) and 0.35 M TEAB (80 ml). The product-containing fraction (0.35 M eluent) was evaporated under reduced pressure. The residue was co-evaporated with water (2×10 ml). The residue was further purified by semi-preparative reverse phase HPLC [HPLC gradient: A, 100% 0.1 M TEAB; B 100% MeCN; 0-2 min, 5% B (flow 2-5 ml/min); 2-15 min, 5-22% B (flow 5 ml/min); 15-21 min, 22-45% B (flow 5 ml/min); 21-22 min, 45-95% B (flow 5 ml/min); 22-25 min, 95% B (flow 5 ml/min); 25-27 min, 95-5% B (flow 5 ml/mm); 27-30 min, 5% B (flow 5-2 ml/min)]. The product with retention time of 19.26 min was collected and evaporated under reduced pressure and the residue was co-evaporated with water (2×5 ml) to give the title compound (2) as triethyl ammonium salt (2.29 μmol, quantification at $\lambda_{max(494)}$ in 0.1 M TEAB buffer, 45.8%). $^1$HNMR of product with Rt 19.26 min in D$_2$O indicated approximately average 5.6 triethylammonium count ions. $^1$H NMR (400 MHz, D$_2$O), δ 1.00 (t, J=7.3 Hz, 51H, CH$_3$, triethylammonium count ion), 2.35 (t, J=5.6 Hz, 2H, CH$_2$), 2.75 (q, J=7.3 Hz, 34H, CH$_2$, triethylammonium count ion), 3.22-3.62 (m, 56H), 3.70-3.78 (m, 1H), 3.79 (s, 2H, OCH$_2$CO$_2$H), 3.87-3.95 (m, 1H), 4.02-4.12 (m, 2H, ArOCH$_2$), 4.90-4.98 (m, 1H, CHN$_3$), 6.78 (d, J=9.3 Hz, 2H, Ar—H), 6.98-7.08 (m, 3H, Ar—H), 7.14-7.22 (m, 2H, Ar—H), 7.28 (t, J=7.9 Hz, 1H, Ar—H), 7.51 (s, 1H, Ar—H), 7.86 (d, J=8.0 Hz, 1H, Ar—H) and 7.91 (d, J=8.0 Hz, 1H, Ar—H). LC-MS (electrospray negative): 740.35 [(M/2e)−1], 493.50 [(M/3e)−1] as monopotassium adduct salt.

7-[3-(-Alexa488-PEG$_{12}$-LN$_3$-linkeracetylamino)-prop-1-ynyl]-3'-azidomethyl-dGTP (3)

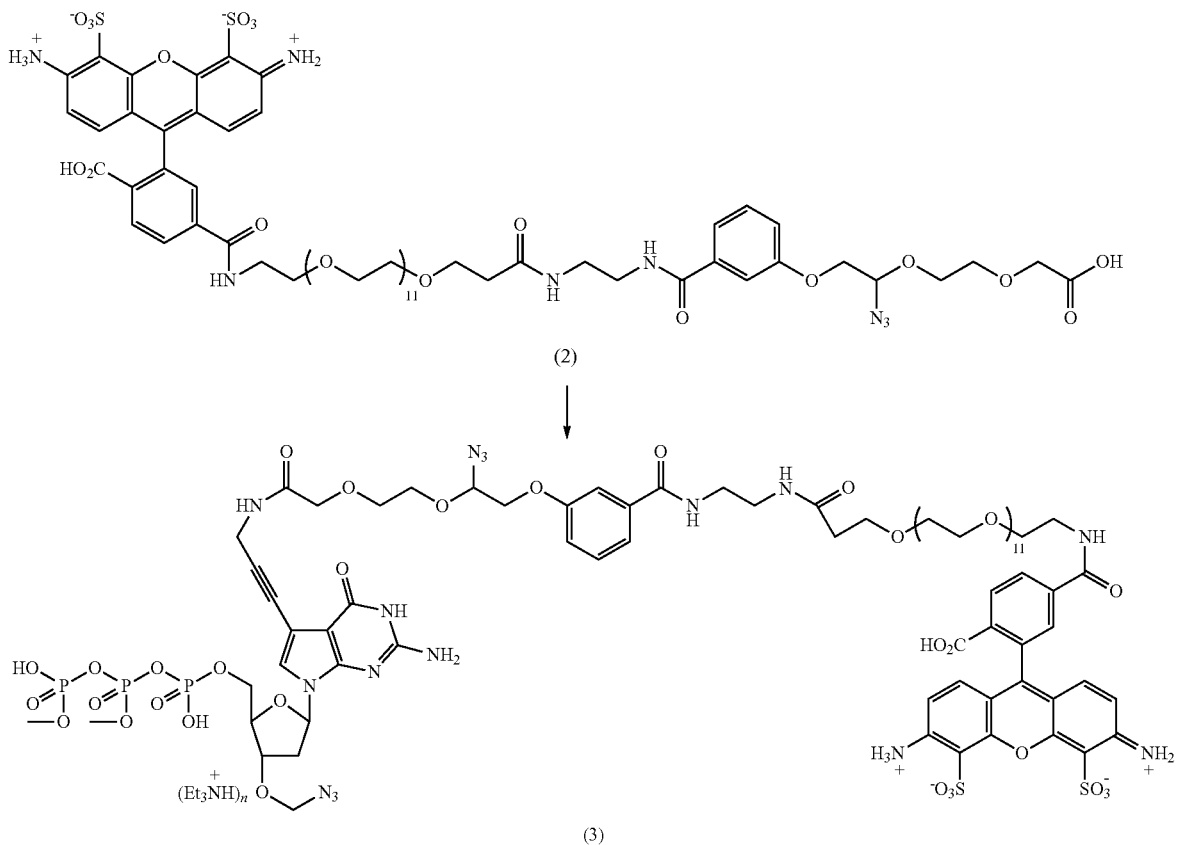

Alexa488-PEG$_{12}$-LN$_3$ linker carboxylic acid (2) (2 μmol) was co-evaporated under reduced pressure with anhydrous DMF (2 ml) and the re-dissolved in anhydrous DMF (0.8 ml). A solution of TSTU (6 μmol, 100 μl, concentration: 18 mg TSTU in 1 ml dry DMF) in dry DMF was added. The reaction was stirred at room temperature for 10 minutes. [7-(3-amino-prop-1-ynyl)]-3'-azidomethyl-dGTP (6 μmol, prepared by evaporating an aqueous solution of [7-(3-amino-prop-1-ynyl)]-3'-azidomethyl-dGTP in 0.1 M TEAB buffer (1.82 ml) and with tri-n-butyl amine (14.3 μl, 60 μmol) in DMF (200 μl)) in 0.1 M TEAB buffer (0.2 ml) was then added. The reaction was stirred at room temperature for 4 hrs, and then diluted with chilled 0.1 M TEAB (4 ml). The whole reaction mixture was then loaded onto a DEAE-A25 Sephadex column (1×10 cm). The column was then eluted with 0.1M (60 ml), 0.3 M (60 ml) and 0.7 M (80 ml) TEAB buffer. The 0.7 M eluent was collected and evaporated under reduced pressure and the residue was co-evaporated with water (2×5 ml). The residue was dissolved in 0.1 M TEAB (5 ml), then further purified by semi-preparative reverse phase HPLC [HPLC gradient: A, 100% 0.1 M TEAB; B 100% MeCN; 0-2 min, 5% B (flow 2-5 ml/min); 2-15 min, 5-22% B (flow 5 ml/min); 15-21 min, 22-25% B (flow 5 ml/min); 21-22 min, 25-95% B (flow 5 ml/min); 22-25 min, 95% B (flow 5 ml/min); 25-27 min, 95-5% B (flow 5 ml/min); 27-30 min, 5% B (flow 5-2 ml/min)]. The product with retention time of 18.49 min was collected and evaporated under reduced pressure to give the title compound (3) as triethyl ammonium salt (1.27 μmol, quantification at $\lambda_{max(494)}$ in 0.1 M TEAB buffer, 63.5%). $^1$HNMR of product with Rt 18.49 min in D$_2$O indicated approximately average 71 triethylammonium count ions. $^1$H NMR (400 MHz, D$_2$O), δ 1.09 (t, J=7.3 Hz, 639H, CH$_3$, triethylammonium count ion), 2.20-2.31 (m, 1H, H$_a$-2'), 2.32 (t, J=5.9 Hz, 2H, CH$_2$), 2.36-2.52 (m, 1H, H$_b$-2'), 3.01 (q, J=7.3 Hz, 426H, CH$_2$, triethylammonium count ion), 3.23-3.59 (m, 54H), 3.61-3.82 (m, 3H), 3.87-4.12 (m, 9H), 4.13-4.18 (m, 1H, H-4'), 4.44-4.50 (m, 1H, H-3'), 4.74-4.80 (m, 2H, OCH$_2$N$_3$), 4.89-4.97 (m, 1H, CHN$_3$), 5.96-6.08 (m, 1H, H-1'), 6.73-6.81 (m, 3H), 6.95 (s, 1H), 7.00-7.15 (m, 5H), 7.49 (s, 1H, Ar—H), and 7.80-7.92 (m, 2H, Ar—H). $^{31}$P NMR (D$_2$O), δ −20.94 (m, $^β$P), −10.08 (d, J=18.6 Hz, $^α$P) and −5.00 (d, J=21.1 Hz, $^γ$P). LC-MS (electrospray negative): 1038.2 [(M/2e)−1].

Example 2

Preparation of 7-[3-(-Alexa488-PEG$_{24}$-LN$_3$-linker-acetylamino)-prop-1-ynyl]-3'-azidomethyl-dGTP (6)

Alexa488-PEG$_{24}$ carboxylic acid (4)

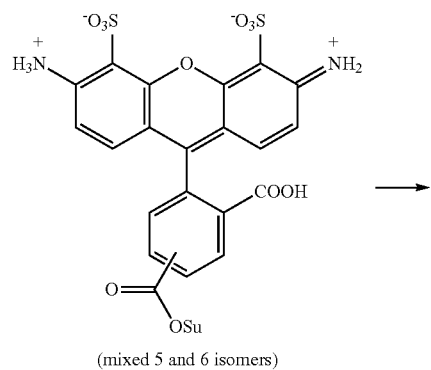

(mixed 5 and 6 isomers)

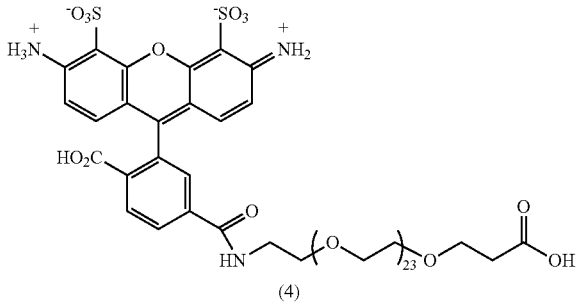

(4)

Alexa fluor 488 carboxylic acid succinimidyl ester (mixed isomers, 10 mg, 15.5 μmoles) was dissolved in dry DMF (2 ml). Amino dPEG$_{24}$ t-butyl ester (41.5 mg, 34.5 μmoles) and DIPEA (69.6 μl, 400 μmoles) were added. The reaction was then stirred at RT for 3 hrs. All the solvents were evaporated under reduced pressure and the residue was then dissolved in a mixture solvent of TFA (2 ml) and DCM (8 ml). The reaction was stirred at room temperature. After 30 minutes, all the solvents were evaporated under reduce pressure. The residue was then diluted with chilled TEAB buffer (0.1 M, 100 ml). The solution was then loaded onto a column of DEAE-A25 Sephadex (2×15 cm). The column was eluted with 0.1 M (50 ml) and 0.3 M (50 ml) TEAB buffer. 0.1 M eluent was discarded. 0.3 M eluent was collected and evaporated under reduced pressure. The residue was co-evaporated with water (2×10 ml) and then further purified by semi-preparative reverse phase HPLC [HPLC gradient: A, 100% 0.1 M TEAB; B 100% MeCN; 0-2 min, 5% B (flow 2-5 ml/min); 2-20 min, 5-25% B (flow 5 ml/min); 20-22 min, 25-95% B (flow 5 ml/min); 22-25 min, 95% B (flow 5 ml/min); 25-27 min, 95-5% B (flow 5 ml/min); 27-30 min, 5% B (flow 5-2 ml/min)]. The first isomer product with retention time of 20.25 min was collected and evaporated under reduced pressure and the residue was co-evaporated with water (2×5 ml) to give the title compound as triethyl ammonium salt (5.5 μmol, quantification at $\lambda_{max(494)}$ in 0.1 M TEAB buffer, 35.4%). This isomer was used to forward synthesis. The second isomer product with retention time 20.62 min was kept aside. $^1$HNMR of product with Rt 20.25 min in D$_2$O indicated approximately 1.5 triethylammonium count ions. $^1$H NMR (400 MHz, D$_2$O), δ 1.12 (t, J=7.3 Hz, 13.5H, CH$_3$, triethylammonium count ion), 2.46 (t, J=6.2 Hz, 2H, CH$_2$), 3.04 (q, J=7.3 Hz, 9H, CH$_2$, triethylammonium count ion), 3.34-3.66 (m, 98H), 6.81 (d, J=9.3 Hz, 2H, Ar—H), 7.08 (d, J=9.3 Hz, 2H, Ar—H), 7.55 (s, 1H, Ar—H) and 7.93 (s, 2H, Ar—H). LC-MS (electrospray negative): 829.75 [(M/2e)−1], 553.25 [(M/3e)−1].

Alexa488-PEG$_{24}$-LN$_3$ linker carboxylic acid (5)

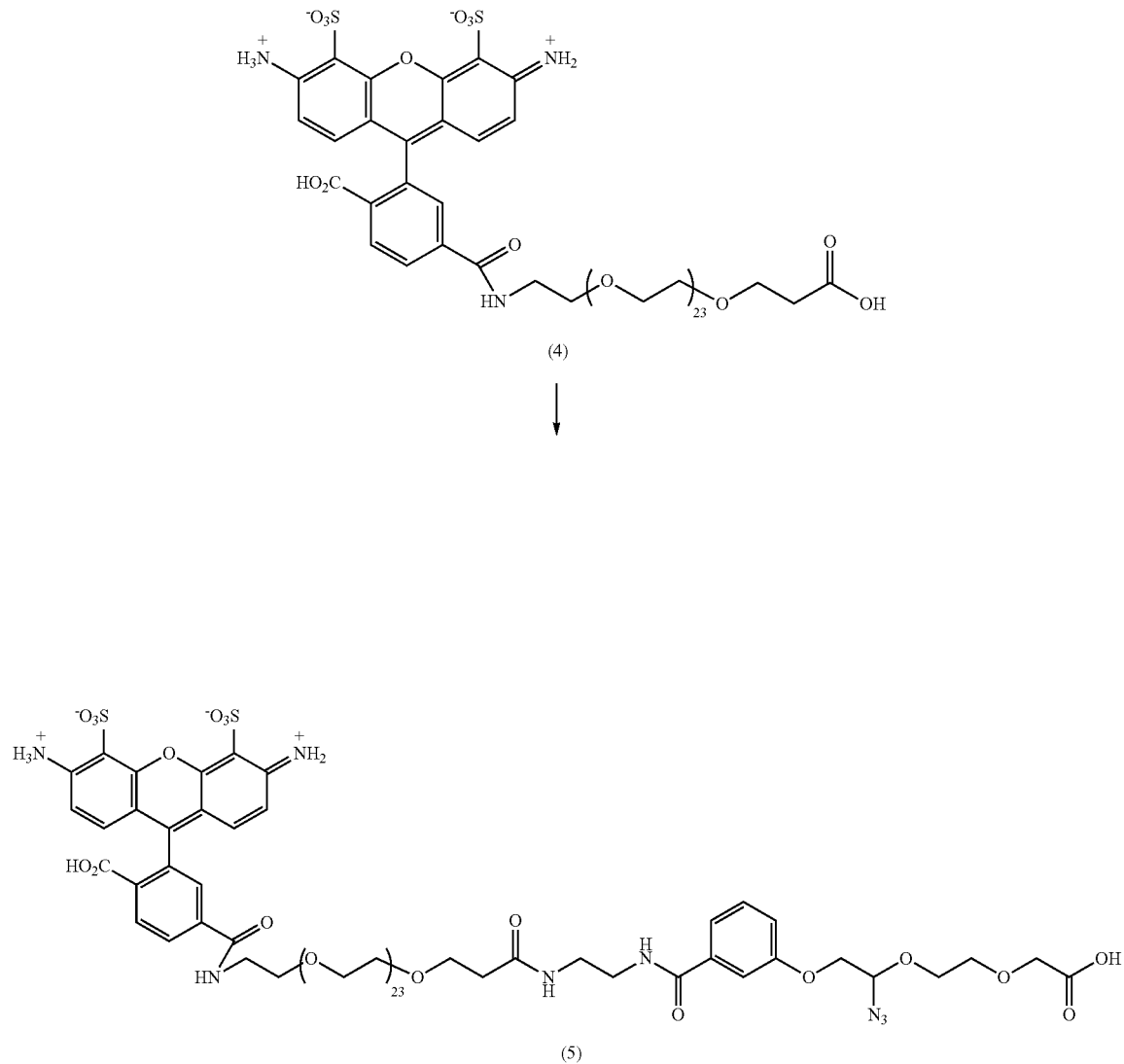

Alexa488-PEG$_{24}$ carboxylic acid (4) (0.6 μmol) was co-evaporated with dry DMF (2 ml) and the residue was then dissolved in dry DMF (1 ml). A solution of TSTU (2.4 μmol, 100 μl, concentration: 7.23 mg TSTU in 1 ml dry DMF) in dry DMF was added. The reaction was stirred at room temperature for 10 minutes. LN$_3$ linker ((2-(2-[3-(2-amino-ethylcarbamoyl)-phenoxy]-1-azido-ethoxy)-ethoxy)-acetic acid) (6 μmol, 2.2 mg) was added followed by DIPEA (30 μmol, 5.2 μl). The reaction was stirred at room temperature. After overnight (18 hrs), the reaction was diluted with chilled 0.1 M TEAB buffer (10 ml) and then loaded onto a DEAE-A25 Sephadex column (1×10 cm). The column was eluted with 0.1 M TEAB (30 ml, this fraction was discarded) and 0.30 M TEAB (50 ml). The product-containing fraction (0.30 M eluent) was evaporated under reduced pressure. The residue was co-evaporated with water (2×5 ml). The residue was further purified by semi-preparative reverse phase HPLC [HPLC gradient: A, 100% 0.1 M TEAB; B 100% MeCN; 0-2 min, 5% B (flow 2-5 ml/min); 2-15 min, 5-22% B (flow 5 ml/min); 15-21 min, 22-50% B (flow 5 ml/min); 21-22 min, 50-95% B (flow 5 ml/min); 22-25 min, 95% B (flow 5 ml/min); 25-27 min, 95-5% B (flow 5 ml/min); 27-30 min, 5% B (flow 5-2 ml/ml)]. The product with retention time of 19.46 min was collected and evaporated under reduced pressure and the residue was co-evaporated with water (2×2 ml) to give the title compound (5) as triethyl ammonium salt (0.224 μmol, quantification at $\lambda_{max(494)}$ in 0.1 M TEAB buffer, 37.3%). $^1$HNMR of product with Rt 19.46 min in D$_2$O indicated approximately average one triethylammonium count ions. $^1$H NMR (400 MHz, D$_2$O), δ1.11 (t, J=7.3 Hz, 9H, CH$_3$, triethylammonium count ion), 2.35 (t, J=5.9 Hz, 2H, CH$_2$), 3.04 (q, J=7.3 Hz, 6H, CH$_2$, triethylammonium count ion), 3.20-3.70 (m, 104H), 3.65-3.78 (m, 1H), 3.80 (s, 2H, OCH$_2$CO$_2$H), 3.85-4.05 (m, 1H), 4.13 (d, J=4.2 Hz, 2H, ArOCH$_2$), 4.96 (t, J=4.3 Hz, 1H, CHN$_3$), 6.80 (d, J=9.4 Hz, 2H, Ar—H), 7.06 (s, 1H, Ar—H), 7.08 (d, J=9.4 Hz, 2H, Ar—H), 7.15-7.25 (m, 2H, Ar—H), 7.32 (t, J=7.8 Hz, 1H, Ar—H), 7.53 (s, 1H, Ar—H), 7.87 (d, J=8.2 Hz, 1H, Ar—H) and 7.91 (d, J=8.2 Hz, 1H, Ar—H). LC-MS (electrospray negative): 669.30 [(M/3e)−1], 501.90 [(M/4e)−1].

7-[3-(-Alexa488-PEG$_{24}$-LN$_3$-linkeracetylamino)-prop-1-ynyl]-3'-azidomethyl-dGTP (6)

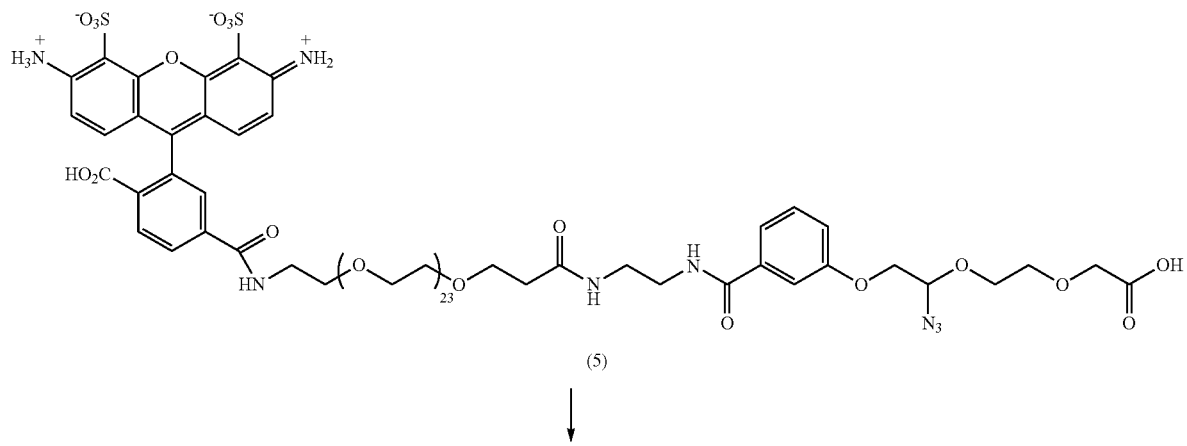

(5)

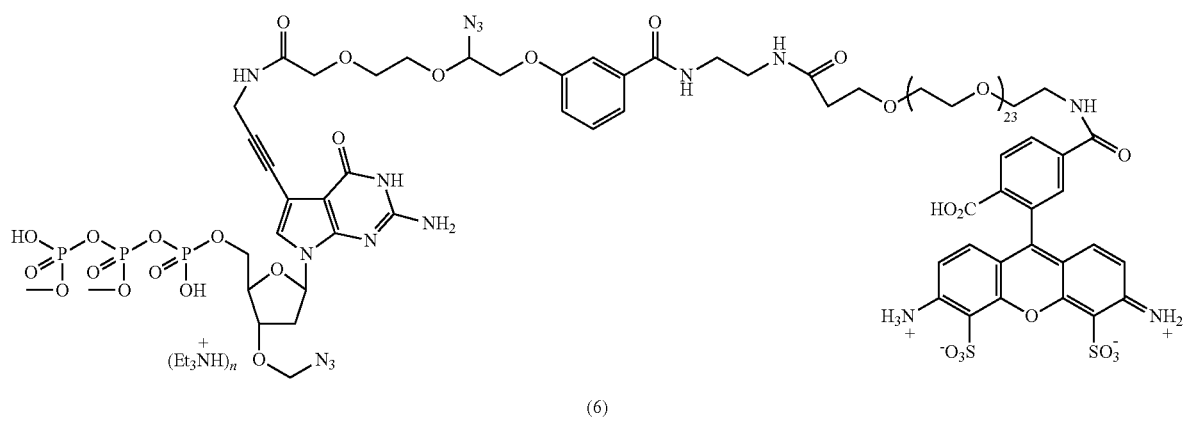

(6)

Alexa488-PEG$_{24}$-LN$_3$ linker carboxylic acid (5) (0.5 µmol) was co-evaporated under reduced pressure with anhydrous DMF (1 ml) and then re-dissolved in anhydrous DMF (0.5 ml). A solution of TSTU (2 µmol, 50 µl, concentration: 12 mg TSTU in 1 ml dry DMF) in dry DMF was added. The reaction was stirred at room temperature for 10 minutes. [7-(3-amino-prop-1-ynyl)]-3'-azidomethyl-dGTP (2.5 µmol) in 0.1 M TEAB buffer (0.2 ml) was then added. The reaction was stirred at room temperature for 3 hrs and stored in fridge overnight (18 hrs). It was then diluted with chilled 0.1 M TEAB (10 ml). The whole reaction mixture was then loaded onto a DEAE-A25 Sephadex column (1×10 cm). The column was then eluted with 0.1M (30 ml), 0.3 M (30 ml) and 0.6 M (50 ml) TEAB buffer. The 0.6 M eluent was collected and evaporated under reduced pressure and the residue was co-evaporated with water (10 ml). The residue was dissolved in 0.1 M TEAB (5 ml), then further purified by semi-preparative reverse phase HPLC [HPLC gradient: A, 100% 0.1 M TEAB; B 100% MeCN; 0-2 min, 5% B (flow 2-5 ml/min); 2-15 min, 5-25% B (flow 5 ml/min); 15-21 min, 25-30% B (flow 5 ml/min); 21-22 min, 30-95% B (flow 5 ml/min); 22-25 min, 95% B (flow 5 ml/min); 25-27 min, 95-5% B (flow 5 ml/min); 27-30 min, 5% B (flow 5-2 ml/min)]. The product with retention time of 19.57 min was collected and evaporated under reduced pressure to give the title compound (6) as triethyl ammonium salt (0.231 µmol, quantification at $\lambda_{max(494)}$ in 0.1 M TEAB buffer, 46.2%). $^1$HNMR of product with Rt 19.57 min in D$_2$O indicated approximately average one triethylammonium count ions. $^1$H NMR (400 MHz, D$_2$O), δ 1.11 (t, J=7.3 Hz, 9H, CH$_3$, triethylammonium count ion), 2.20-2.24 (m, 1H, H$_a$-2') 2.35 (t, J=5.8 Hz, 2H, CH$_2$), 2.38-2.48 (m, 1H, H$_b$-2'), 3.03 (q, J=7.3 Hz, 6H, CH$_2$, triethylammonium count ion), 3.40-3.60 (m, 102H), 3.65-3.85 (m, 3H), 3.87-4.11 (m, 9H), 4.12-4.20 (m, 1H, H-4'), 4.49-4.51 (m, 1H, H-3'), 4.77-4.82 (m, 2H, OCH$_2$N$_3$), 4.85-5.00 (m, 1H, CHN$_3$), 6.00-6.20 (m, 1H, H-1'), 6.73-6.85 (m, 3H), 6.96 (s, 1H), 7.05-7.18 (m, 5H), 7.52 (d, J=1.4 Hz 1H, Ar—H), 7.80 (d, J=8.1 Hz, 1H, Ar—H) and 7.90 (dd, J=1.5 and 8.1 Hz, 1H, Ar—H). LC-MS (electrospray negative): 1302.9 [(M/2e)−1].

Comparative Example

Synthesis of 7-[3-(-Alexa488-LN$_3$-linker acetylamino)-prop-1-ynyl]-3'-azidomethyl-dGTP (8)

Alexa488-LN$_3$ linker carboxylic acid (7)

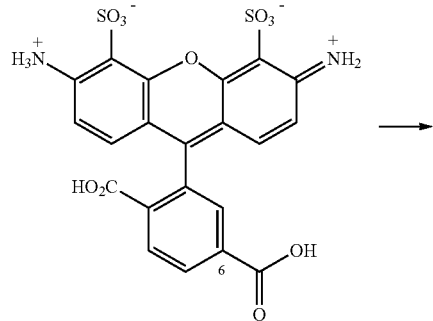

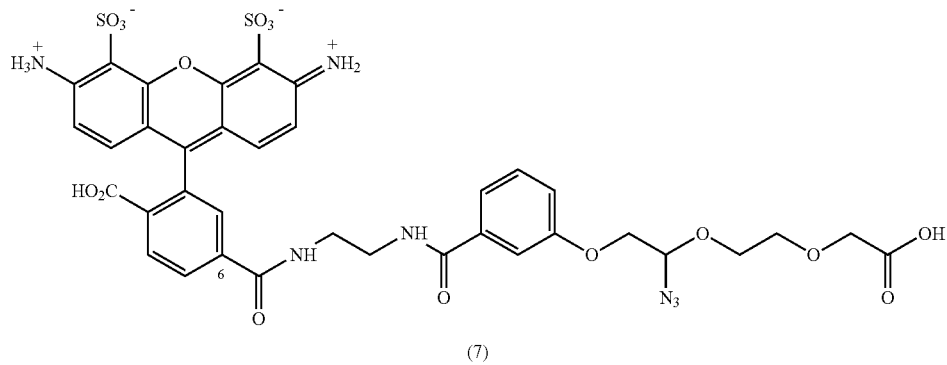

(7)

Alexa flour 488 6-carboxylic acid (9 μmol) was stirred with N,N'-di-succinimidyl carbonate (19.8 μmol, 5.07 mg), DMAP (19.8 μmol, 2.42 mg) and DIPEA (30 μmol, 5.23 μl) in dry DMF (1 ml). After 15 minutes at room temperature, LN$_3$ linker ((2-{2-[3-(2-amino-ethylcarbamoyl)-phenoxy]-1-azido-ethoxy}-ethoxy)-acetic acid) (30 μmol, 11.0 mg) was added followed by DIPEA (60 μmol, 10.45 μl). The reaction was stirred at room temperature overnight (18 hrs). The reaction was then diluted with chilled water (15 ml) and then loaded onto a DEAE-A25 Sephadex column (1×10 cm). The column was eluted with 0.1 M TEAB (50 ml, this fraction was discarded) and 1.0M TEAB (50 ml). The product-containing fraction (1.0 M eluent) was evaporated under reduced pressure. The residue was co-evaporated with water (2×10 ml). The residue was further purified by preparative HPLC [HPLC gradient: A, 100% 0.1 M TEAB; B 100% MeCN; 0-2 min, 5% B (flow 2-10 ml/min); 2-19 min, 5-25% B (flow 10 ml/min); 19-21 min, 25-95% B (flow 10 ml/min); 21-24 min, 95% B (flow 10 ml/min); 24-26 min, 95-5% B (flow 10 ml/min); 26-30 min, 5% B (flow 10-2 ml/min)]. The product with retention time of 20.06 min was collected and evaporated under reduced pressure and the residue was co-evaporated with water (2×5 ml) to give the title compound (7) as triethyl ammonium salt (3.69 μmol, quantification at $\lambda_{max}$ (495) in 0.1 M TEAB buffer, 51%; also recovered 1.76 μmole Alexa flour 488 6-carboxylic acid). $^1$HNMR of product in D$_2$O indicated approximately average 3.7 triethylammonium count ions. $^1$H NMR (400 MHz, D$_2$O), δ 1.08 (t, J=7.3 Hz, 33H, CH$_3$, triethylammonium count ion), 2.94 (q, J=7.3 Hz, 22H, CH$_2$, triethylammonium count ion), 3.45-3.65 (m, 6H), 3.68-3.78 (m, 1H), 3.79 (s, 2H, OCH$_2$CO$_2$H), 3.87-3.93 (m, 2H), 3.95-4.05 (m, 1H), 4.84 (t, J=4.0 Hz, 1H, CHN$_3$), 6.69 (d, J=9.3 Hz, 1H, Ar—H), 6.72 (d, J=9.3 Hz, 1H, Ar—H), 6.84 (d, J=9.3 Hz, 1H, Ar—H), 6.85-6.94 (m, 2H, Ar—H), 6.95-7.04 (m, 2H, Ar—H), 7.07 (t, J=7.9 Hz, 1H, Ar—H), 7.13 (s, 1H, Ar—H), 7.81 (d, J=8.1 Hz, 1H, Ar—H) and 7.84 (d, J=8.1 Hz, 1H, Ar—H). LC-MS (electrospray negative): 882.80 [M−1].

7-[3-(-Alexa488-LN₃-linkeracetylamino)-prop-1-ynyl]-3'-azidomethyl-dGTP (8)

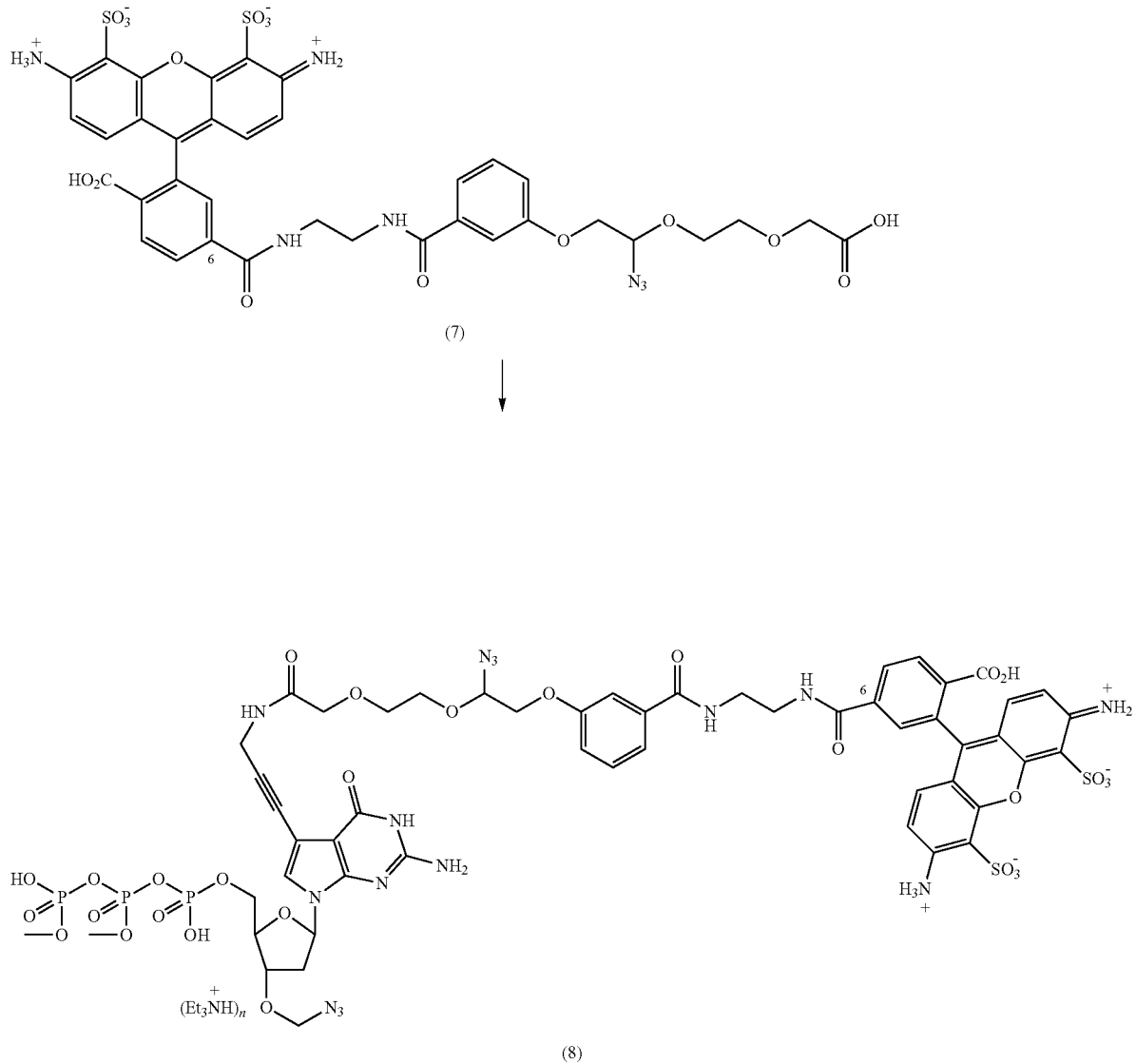

Alexa flour 488 LN₃ linker carboxylic acid (7) (1.65 µmol) was dissolved in dry DMF (0.5 ml). N,N'-di-succinimidyl carbonate (5.4 µmol, 1.38 mg) and DMAP (3.6 µmol, 0.44 mg) were added. After 15 minutes at room temperature, all the above reaction mixture was added to [7-(3-amino-prop-1-ynyl)]-3'-azidomethyl-dGTP (5.8 µmol, prepared by evaporating an aqueous solution of [7-(3-amino-prop-1-ynyl)]-3'-azidomethyl-dGTP in 0.1 M TEAB buffer (1.45 ml) and with tri-n-butyl amine (144 µl)). The reaction was stirred at room temperature 3 hrs. The reaction was then diluted with chilled 0.1 M TEAB (10 ml) and then loaded onto a DEAE-A25 Sephadex column (1×8 cm). The column was eluted with 0.1 M (50 ml, this reaction was discarded) and 2.0 M TEAB (50 ml). The product-containing fraction (2.0 M eluent) was evaporated under reduced pressure. The residue was co-evaporated with water (2×5 ml). The residue was further purified by semi-preparative reverse phase HPLC [HPLC gradient: A, 100% 0.1 M TEAB; B 100% MeCN; 0-2 min, 5% B (flow 2-5 ml/min); 2-14 min, 5-20% B (flow 5 ml/min); 14-20 min, 20-23% B (flow 5 ml/min); 20-22 min, 23-95% B (flow 5 ml/min); 22-25 min, 95% B (flow 5 ml/min); 25-26 min, 95-5% B (flow 5 ml/min); 26-30 min, 5% B (flow 5-2 ml/min)]. The product with retention time of 16.63 min was collected and evaporated under reduced pressure and the residue was co-evaporated with water (5 ml) to give the title compound (8) as triethyl ammonium salt (0.257 µmol, quantification at $\lambda_{max(495)}$ in 0.1 M TEAB buffer, 15.6%). ¹H NMR (400 MHz, D₂O), 2.14-2.30 (m, 1H, H$_a$-2'), 2.38-2.52 (m, 1H, H$_b$-2'), 3.49-4.02 (m, 16H), 4.15-4.25 (m, 1H), 4.45-4.55 (m, 1H), 4.80 (d, J=6.9 Hz, 1H, Ar—OCH$_a$H$_b$), 4.84 (d, J=6.9 Hz, 1H, Ar—OCH$_a$H$_b$), 4.87-4.92 (m, 1H, CHN₃), 5.86-5.95 (m, 1H), 6.54 (t, J=9.1 Hz, 1H, Ar—H), 6.62-6.67 (m, 1H, Ar—H), 6.70 (d, J=8.0 Hz, 1H, Ar—H), 6.78-6.83 (m, 2H, Ar—H), 6.87-7.04 (m, 4H, Ar—H), 7.39 (s, 1H, Ar—H) and 7.81-7.90 (m, 2H, Ar—H). MS (electrospray negative): 757.40 [(M/2e)−1], 505.00 [(M/3e)−1] (as mono potassium adduct salt).

Example 3

Preparation of Atto532-Peg12-LN3-dGTP

Step 1
Synthesis of Atto532-Peg12

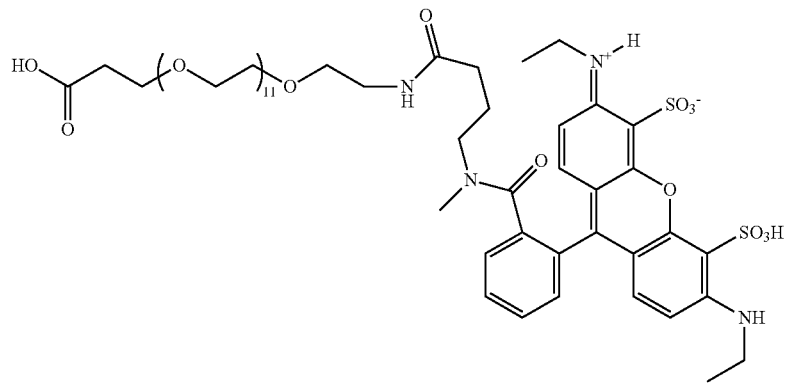

Atto532NHS ester (20 mg, 26.9 μmol) (Atto-tec AD532-3) was dissolved in DMF (1.5 ml). A solution of H2N-PEG12-COOH (49.8 mg, 80.7 μmol) in 0.1 M TEAB (0.5 ml) was added to the reaction. The reaction was monitored by TLC (eluting system ACN: $H_2O$ 4:1) and reached completion in 90 min. It was quenched with 2 ml of 0.1 M TEAB and concentrated to dryness. The crude was purified by doing a Sephadex column (1×10 cm). We eluted three fractions, first with 40 ml of 0.1 M TEAB, second with 100 ml of 0.3H TEAS and finally with 100 ml of 0.5 N TEAB. The product of the reaction was contained in fraction 2. This was submitted to HPLC purification (5-50 method in 20 min in the semiprep Zorbax column), retention time 13.7 min. The product was obtained in 64% yield.

MS (es−, m/z): 1243, 622

1H NMR (400 MHz; $D_2O$) 7.65-7.56 (2H, m, CHar, CHar), 7.52-7.45 (1H, m, CHar), 7.40-7.36 (1H, m, CHar), 7.23-7.18 (2H, m which includes doublet, J 9.6, CHar, CHar), 6.92 (1H, d, J 9.6 CHar), 6.91 (1H, d, J 9.6, CHar), 3.58 (2H, t, J 6.8, $CH_2$), 3.55-3.45 [44H, m, 11×(O—$CH_2$)+11×($CH_2$—O)], 3.40 (2H, t, J 5.6, $CH_2$), 3.33 (4H, q, J 7.2, 2×$CH_2$), 3.19 (1H, t, J 5.6, CH), 3.14 (1H, t, J 5.6, CH), 3.09 (1H, br.t, CH), 2.78 (3H, s, $CH_3$), 2.31 (2H, t, J 6.8, $CH_2$), 1.60-1.52 (2H, m, $CH_2$), 1.32-1.24 (2H, m, $CH_2$), 1.17 (6H, t, J 7.2, 2×$CH_3$).

Step 2
Preparation of Atto532-PEG12-LN3

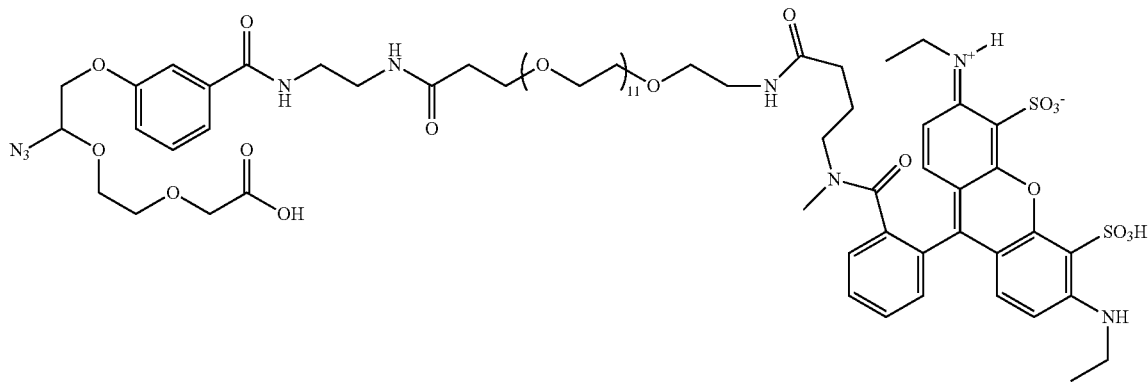

Atto532PEG (21.6 mg, 17.4 μmol) was dissolved in DMF (1.8 ml). A solution of TSTU (7.8 mg, 26.1 μmol) in DMF was added to the reaction. Since not much progress was observed after 30 min by TLC (eluting system ACN: H$_2$O 4:1), DIPEA (15 μl, 87 μmol) was added. The activation was completed in 30 min and LN3 (15.9 mg, 43.5 μmol) dissolved in DMF was added. The reaction was left stirring for 16 h, after which it was quenched with 10 ml of 0.1 M TEAB and vacuumed off. The reaction crude was purified by HPLC (5-50 method in 20 min in the semiprep Zorbax column), retention time 14.9 min. The product was obtained in 66 yield.

MS (es−, m/z): 796

1H NMR (400 MHz; D$_2$O) 7.66-7.56 (2H, m, CHar, CHar), 7.54-7.45 (1H, m, CHar), 7.38-7.34 (1H, m, CHar), 7.28 (1H, q, J 8.0, CHar), 7.23-7.15 (4H, m, CHar), 7.08-7.01 (1H, br.d, J 8.0, CHar), 6.90 (1H, d, J 5.2, CHar), 6.88 (1H, d, J 5.2, CHar), 4.94 (1H, t, J 4.4, CHN$_3$), 4.12 (2H, br.d, J 4.0, CH$_2$), 4.00-3.86 (2H, double m, CHH), 3.81 (2H, s, O—CH$_2$), 3.81-3.72 (1H, m, CHH), 3.63-3.55 (5H, m, 2×CH$_2$+CH), 3.54-3.26 [53H, triple m, 4×CH$_2$+CH+11×(O—CH$_2$)+11×(CH$_2$—O)], 3.22-3.12 (2H, m, CH$_2$), 2.76 (3H, s, CH$_3$), 2.35 (2H, t, J 5.6, CH$_2$), 1.96-1.90 (1H, m, CH), 1.60-1.49 (1H, m, CH), 1.31-1.22 (1H, m, CH$_2$), 1.17 (6H, t, J 7.2, 2×CH$_3$).

Step 3
Synthesis of G-Atto532-PEG12-LN3

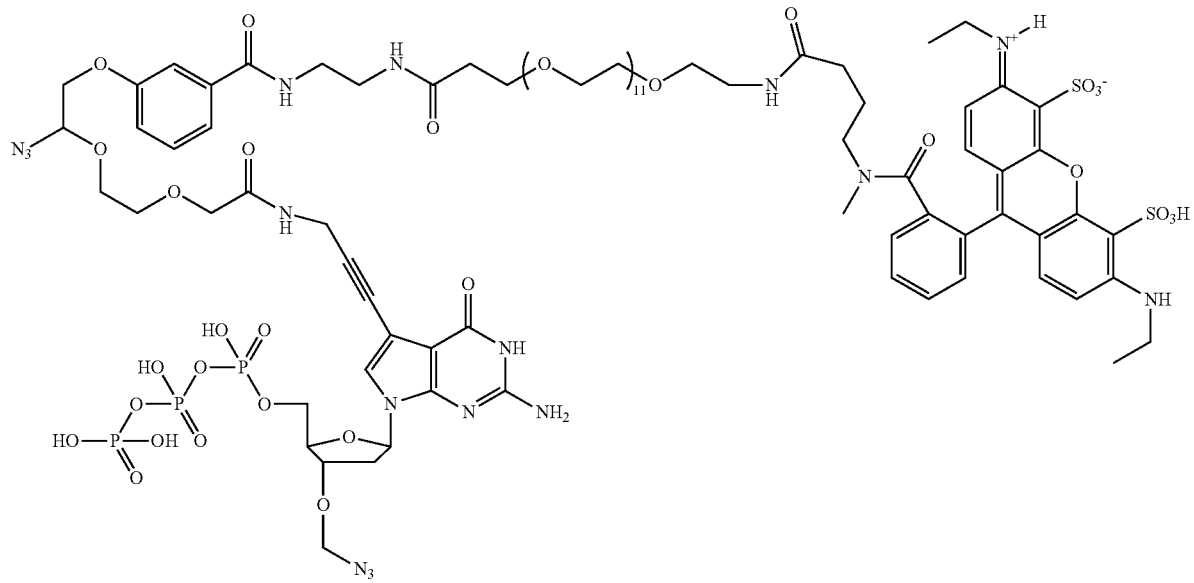

Atto532PEGLN3 (18 mg, 11.3 μmol) was dissolved in DMF (3 ml). A solution of TSTU (5.1 mg, 17 μmol) in DMF (200 μl) was added. The progress of the reaction was monitored by TLC (eluting system ACN: H2O 4:1). No activation is observed after 30 min, so DIPEA (10 μl) was added. After 30 min, the TLC shows that the activation was completed. PPPG (34 μmol, 2.25 mM) was co-evaporated with tributylamine (81 μl) and redissolved in 0.1 M TEAS (0.5 ml). After 30 min, TLC showed that the reaction had gone to completion (eluting system ACN: H2O 4:1). The reaction was quenched with 10 ml of 0.1 M TEAS at 0° C. and vacuumed off. The reaction crude was purified by HPLC (5-50 method in 20 min in the semiprep Zorbax column), retention time 14.8 min. The product was obtained in 57% yield.

MS (es−, m/z): 1095, 729, 546

1H NMR (400 MHz; D$_2$O) 7.64-7.60 (2H, m, CHar), 7.51-7.44 (1H, m, CHar), 7.35-7.31 (1H, m, CHar), 7.16-7.12 (4H, m, CHar), 7.09 (1H, s, CHbase), 6.99-6.96 (1H, br.s, CHar), 6.88 (1H, d, J 4.0, CHar), 6.86 (1H, d, J 4.0, CHar), 6.83-6.77 (1H, m, CHar), 6.06-5.96 (1H, m, H-1'), 4.96 (1H, br.s, CHHN$_3$), 4.82 (1H, br.s, CHHN$_3$), 4.54-4.46 (1H, m, H-3'), 4.20-4.14 (1H, m, H-4'), 4.12-3.89 (8H, double m, 3×CH$_2$+2H-5'), 3.86-3.60 (4H, m, CH$_2$+CH$_2$—N), 3.56 (2H, t, J 6.0, CH$_2$), 3.54-3.28 [56H, set m, 11×(O—CH$_2$)+11×(CH$_2$—O)+6CH$_2$], 3.18 (2H, t, J 5.6, CH$_2$), 2.74 (3H, s, CH$_3$), 2.46-2.23 (4H, m+t+m, J 6.0, 2H-2'+CH$_2$), 1.61-1.34 (3H, m, CH$_2$+CH), 1.29-1.14 (3H, m+t, J 7.2, CH$_2$+2×CH$_3$).

Example 4

Demonstration of Reduced Quenching of Fluorophores in Modified Nucleotides of the Invention The modified nucleotides of Examples 1 and 2 ((3) and (6)) and the compound of the Comparative Example (8) described above were each incorporated into a polynucleotide by phosphodiester linkage of the modified nucleotide to the 3' end of a DNA strand, the precise sequence of which is not of relevance. The fluorescent intensity of the Alexa 488 dye in the modified nucleotides was then measured, both before and after treatment with Tris-(2-carboxyethyl)phosphine (TCEP). FIG. 1 shows the intensity measured of the Alexa 488 dye, for all three modified nucleotides, both before and after cleavage of the linkers with TCEP. The modified nucleotide of the comparative example (i.e. G-N3-A488 with no PEG in the linker) clearly shows the highest level of quenching (i.e. lowest fluorescence intensity) before TCEP cleavage. However, the similarity in fluorescence intensity measured after cleavage of all three linkers is striking. Since the point of cleavage in the chain leaves the PEG moieties still attached to the Alexa 488 fluorophore, this experiment demonstrates that because the "free" fluorophore (i.e. without the guanine base) is not quenched in solution, the enhanced signal in the fully functionalised nucleotides (ff's) of the invention is not simply an artefact of the PEG moiety being attached to the fluorophore. The FIGURE also illustrates that compound (6) demonstrates a greater reduction in quenching (i.e. higher fluorescence intensity before TCEP treatment) over not only the modified nucleotides of the comparative example, but also over compound (3).

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

The invention claimed is:

1. A modified nucleoside, comprising a base attached to a fluorophore through a cleavable linking group, wherein the cleavable linking group comprises a cleavable functionality and a hydrophilic spacer group of 5 to 150 atoms.

2. The modified nucleoside of claim 1, wherein the base is a modified guanine.

3. The modified nucleoside of claim 1, wherein the base is guanine.

4. The modified nucleoside of claim 1, further comprising at least one phosphate group.

5. The modified nucleoside of claim 4, wherein the modified nucleoside is a modified nucleotide triphosphate.

6. The modified nucleoside of claim 1, wherein the cleavable functionality comprises azide.

7. The modified nucleoside of claim 6, wherein the cleavable functionality is cleaved using a phosphine.

8. The modified nucleoside of claim 1, wherein the cleavable functionality comprises an acetal that has an allyl-cleavable functionality.

9. The modified nucleoside of claim 8, wherein the acetal is cleaved with a transition metal complex.

10. The modified nucleoside of claim 9, wherein the transition metal complex comprises palladium.

11. The modified nucleoside of claim 9, wherein the transition metal complex comprises a transition metal selected from the group consisting of platinum, rhodium, ruthenium, osmium, and iridium.

12. The modified nucleoside of claim 8, wherein the acetal comprises an allyloxy group.

13. The modified nucleoside of claim 8, wherein the acetal comprises an allyl moiety selected from the group consisting of an allylamino group, an allylthioether group, an allyl carbamate group, an allylurea group, and an S-allylthiocarbamate group.

14. The modified nucleoside of claim 1, wherein the cleavable functionality is cleaved by a linker-cleavage method selected from the group consisting of electrophilic cleavage, nucleophilic cleavage, photochemical cleavage, reductive cleavage, oxidative cleavage, safety-catch cleavage, and elimination-mediated cleavage.

15. A kit, comprising the modified nucleoside according to claim 1.

16. A method for detecting a modified nucleoside that has been incorporated into a polynucleotide, comprising:
(a) incorporating the modified nucleoside of claim 1 into a polynucleotide; and
(b) detecting a fluorescent signal from the modified nucleoside that was incorporated in step (a).

17. The method of claim 16, further comprising providing a template nucleic acid strand and a partially hybridized nucleic acid strand,
wherein step (a) incorporates into the hybridized strand at least one modified nucleoside that is complementary to a nucleoside at the corresponding position of the template strand, and
wherein step (b) identifies the base of the incorporated modified nucleoside, thereby indicating the identity of the complementary nucleoside of the template strand.

18. The method of claim 16, wherein step (a) further comprises providing a second modified nucleoside that has a different base and a distinguishable fluorescent signal.

19. A reagent for modifying the base of a nucleoside, comprising a fluorophore and a cleavable linking group, wherein the linking group comprises a cleavable functionality and a hydrophilic spacer group of 5 to 150 atoms.

* * * * *